(12) United States Patent
Hong et al.

(10) Patent No.: US 11,230,539 B2
(45) Date of Patent: *Jan. 25, 2022

(54) 2,3-DIHYDRO-ISOINDOLE-1-ONE DERIVATIVE AS BTK KINASE SUPPRESSANT, AND PHARMACEUTICAL COMPOSITION INCLUDING SAME

(71) Applicant: CrystalGenomics, Inc., Gyeonggi-do (KR)

(72) Inventors: Yong Rae Hong, Gyeonggi-do (KR); Jeong Eun Na, Gyeonggi-do (KR); Im Sook Min, Gyeonggi-do (KR); Hyun Ju Cha, Seoul (KR); Sool Ki Kwon, Gyeonggi-do (KR); Seonggu Ro, Seoul (KR); Joong Myung Cho, Seoul (KR)

(73) Assignee: CrystalGenomics, Inc., Gyeonggi-Do (KR)

( * ) Notice: Subject to any disclaimer, the term of this patent is extended or adjusted under 35 U.S.C. 154(b) by 35 days.

This patent is subject to a terminal disclaimer.

(21) Appl. No.: 16/791,753

(22) Filed: Feb. 14, 2020

(65) Prior Publication Data

US 2021/0009565 A1    Jan. 14, 2021

Related U.S. Application Data

(63) Continuation of application No. 15/691,432, filed on Aug. 30, 2017, now Pat. No. 10,604,508, which is a continuation of application No. 14/655,954, filed as application No. PCT/KR2013/012204 on Dec. 26, 2013, now Pat. No. 9,758,508.

(60) Provisional application No. 61/746,980, filed on Dec. 28, 2012.

(51) Int. Cl.
| | |
|---|---|
| *A61K 31/4035* | (2006.01) |
| *A61K 31/4178* | (2006.01) |
| *A61K 45/06* | (2006.01) |
| *C07D 403/10* | (2006.01) |
| *C07D 403/04* | (2006.01) |
| *C07D 233/58* | (2006.01) |
| *A61P 35/00* | (2006.01) |

(52) U.S. Cl.
CPC ........ *C07D 403/10* (2013.01); *A61K 31/4178* (2013.01); *A61K 45/06* (2013.01); *A61P 35/00* (2018.01); *C07D 403/04* (2013.01)

(58) Field of Classification Search
CPC ............ A61K 31/4035; A61K 31/4178; A61K 45/06; C07D 403/10; C07D 403/04; C07D 233/58; A61P 35/00
USPC ..... 514/397, 414, 416, 418; 548/312.1, 511, 548/466, 472, 397
See application file for complete search history.

(56) References Cited

U.S. PATENT DOCUMENTS

| | | | |
|---|---|---|---|
| 6,544,985 B2 | 4/2003 | Adam et al. | |
| 9,758,508 B2 | 9/2017 | Hong et al. | |
| 2007/0161648 A1 | 7/2007 | Hughes et al. | |
| 2015/0119421 A1 | 4/2015 | Jain | |
| 2015/0336934 A1 | 11/2015 | Hong et al. | |
| 2017/0362205 A1 | 12/2017 | Hong et al. | |

FOREIGN PATENT DOCUMENTS

| | | |
|---|---|---|
| EP | 1880993 A1 | 1/2008 |
| EP | 2108642 A1 | 10/2009 |
| RU | 2007131274 A | 2/2009 |
| WO | WO 2004/108672 A1 | 12/2004 |
| WO | WO 2007/047646 A2 | 4/2007 |
| WO | WO 2007/107469 A1 | 9/2007 |
| WO | WO 2009/053269 A1 | 4/2009 |
| WO | WO 2012/014017 A1 | 2/2012 |
| WO | WO 2012/047017 A2 | 4/2012 |

OTHER PUBLICATIONS

Extended European Search Report for European Patent Application No. 18190153.9, dated Oct. 10, 2018, 10 pages.
International Search Report and Written Opinion (including English Translations) of International Search Report for International Application No. PCT/KR2013/012204, dated Apr. 30, 2014, 18 pages.
International Preliminary Report on Patentability for International Application No. PCT/KR2013/012204, dated Jun. 30, 2015, 6 pages.
Supplementary European Search Report and the European Search Opinion for EP 13867650.7, dated May 25, 2016, 7 pages.
Barltrop et al., "5-(3-carboxymethoxphenyl)-2-(4,5-dimethylthiazolyl)-3-(4-sulfophenyl)Tetrazolium, Inner Salt (MTS) and Related Analogs of 3-(4,5-dimethylthiazolyl)-2,5-Diphenyltetrazolium Bromide (MTT) Reducing to Purple Water-Soluble Formazans as Cell-Viability Indicators", Bioorganic & Medicinal Chemistry Letters, 1(11):611-614 (1991).
Cory et al., "Use of an Aqueous Soluble Tetrazolium/Formazan Assay for Cell Growth Assays in Culture", Cancer Communications, 3(7): 207-212 (1991).
Heinonen et al., "Silencing of Bruton's Tyrosine Kinase (Btk) Using Short Interfering RNA Duplexes (siRNA)", FEBS Letters, 527(1-3): 274-278 (2002).

(Continued)

*Primary Examiner* — Joseph R Kosack
*Assistant Examiner* — Sagar Patel
(74) *Attorney, Agent, or Firm* — Cooley LLP

(57) ABSTRACT

The present invention provides a compound selected from the group consisting of a compound of formula (I), pharmaceutically acceptable salts, esters, prodrugs, hydrates, solvates and isomers thereof; a use of the compound for the treatment, relief or prevention of diseases caused by absormal or uncontrolled activation of protein kinase, and a use of the compound for the manufacture of a medicament for the treatment, relief or prevention of the diseases; a pharmaceutical composition comprising the compound as an active ingredient; and a method for the treatment, relief or prevention of the diseases using the compound. The inventive compound is useful for the treatment, relief or prevention of diseases caused by abnormal or uncontrolled activation of protein kinase.

22 Claims, No Drawings

(56) References Cited

OTHER PUBLICATIONS

Kawakami et al., "Redundant and Opposing Functions of Two Tyrosine Kinases, Btk and Lyn, in Mast Cell Activation", The Journal of Immunology, 165(3): 1210-1219 (2010).
Database Reaxys, Database accession No. 14139755 (XRN) for U.S. Pat. No. 6,544,985, "Dihydro-benzo [b][1,4]diazepin-2-one derivatives." Database Reaxys (2018); XP002784835, 2 pages.
Database Reaxys, Database accession No. 25131744, 25131745, 25131750-25131752, 25131754, 25131755, 25131760, 25131765-25131767, 25131775, 25131776, 25131781, 25131795-25131798, 25131800, 25131802, 25131803, 25131804, 251318006, 25131807, 25131809, 25131816 and 25131817(XRN) for WO 2012/047017 A2, "2,3-Dihydro-Isoindol-1-One Derivative and a Composition Comprising the Same." Database Reaxys (2018); XP002784834, 6 pages.

2,3-DIHYDRO-ISOINDOLE-1-ONE DERIVATIVE AS BTK KINASE SUPPRESSANT, AND PHARMACEUTICAL COMPOSITION INCLUDING SAME

CROSS-REFERENCE TO RELATED APPLICATIONS

This application is a continuation of U.S. patent application Ser. No. 15/691,432, filed Aug. 30, 2017, which is a continuation of U.S. patent application Ser. No. 14/655,954, filed Jun. 26, 2015, which is the national stage entry of PCT/KR2013/012204, filed Dec. 26, 2013, which claims priority to U.S. Provisional Application No. 61/746,980, filed Dec. 28, 2012.

FIELD OF THE INVENTION

The present invention relates to a compound selected from the group consisting of a compound of formula (I) and pharmaceutically acceptable salts, esters, prodrugs, hydrates, solvates and isomers thereof, and a pharmaceutical composition comprising same as an active ingredient for the treatment, relief or prevention of diseases caused by abnormal or uncontrolled activation or protein kinase.

BACKGROUND OF THE INVENTION

Bruton's tyrosine kinase (BTK) is a member of the TEC family of nonreceptor tyrosine kinases, which consists of 650 amino acid residues and contains pleckstrin homology (PH) domain, zinc-finger region, SH3 domain, SH2 domain, and kinase domain. Recently, kinase domain, among said domains, is gaining more interests as a drug target.

BTK is found in B-cells and hematopoietic cells, rather than some T-cells, natural killer cells, plasma cells, etc. When BTK is stimulated by the B-cell membrane receptor (BCR) signals that are caused by various inflammatory responses or cancers, BTK plays an important role in production of cytokines such as TNF-α, IL-6, etc., as well as NF-κB by initiating downstream signaling such as phospholipase C gamma 2 (PLCγ2).

In the treatment of inflammation, BTK is known for mediating responses of the membrane receptors, e.g., B-cell antigen receptors which detect inflammation-inducing substances, CD40, TLR-4, Fcg and the like. Also, BTK has a strong influence on the signaling mechanism of inflammation caused by stimulation of mast cell, B-cell and macrophage. Therefore, inhibition of BTK may block IgE signaling which may slow down the progression of diseases caused by abnormal activation of BTK. This signaling mechanism is a complicated signaling pathway of immunosubstance secretion. In this process, protein phosphorylation and dephosphorylation take place in a multi-step procedure, and since BTK is one of the high-level steps in the signaling pathway, along with spleen tyrosine kinase (SYK) and, thus, it is more effective for preventing activation of factors that cause immune responses than other kinase targets.

Further, in the treatment of cancer, it is known that BTK modifies BCR and B-cell surface proteins which generate antisuicide signals. Thus, inhibition of BTK may bring about anticancer effects against cancers that are associated with BCR signaling such as lymphoma. In fact, Ibrutinib (PCI-32765) developed by Pharmacyclics Inc. was recently approved as an anti-cancer agent for the treatment of chronic lymphocytic leukemia (CLL), and a phase III trial of AVL-292 developed by Avila Therapeutics for small lymphocytic leukemia (SLL) and CLL is currently underway. It has been proven that these compounds are quite effective against SLL and CLL that are relatively rare type of cancers. However, they have failed to achieve satisfactory results against diffuse large B-cell lymphoma (DLBCL) which is more prevalent type of lymphoma. Thus, there is a growing demand for a noble drug.

The action mechanism of BTK inhibitor as an anti-inflammatory agent as well as an anti-cancer agent is thoroughly described in the reference [Nature Chemical Biology 7, (2011), 4].

SUMMARY OF THE INVENTION

Accordingly, it is an object of the present invention to provide a compound selected from the group consisting of a compound of formula (I), pharmaceutically acceptable salts, esters, prodrugs, hydrates, solvates and isomers thereof.

It is another object of the present invention to provide a pharmaceutical composition comprising same as an active ingredient for the treatment, relief or prevention of diseases caused by abnormal or uncontrolled activation of protein kinase.

In accordance with an aspect of the present invention, there is provided a compound selected from the group consisting of a compound of formula (I) below and pharmaceutically acceptable salts, esters, prodrugs, hydrates, solvates and isomers thereof:

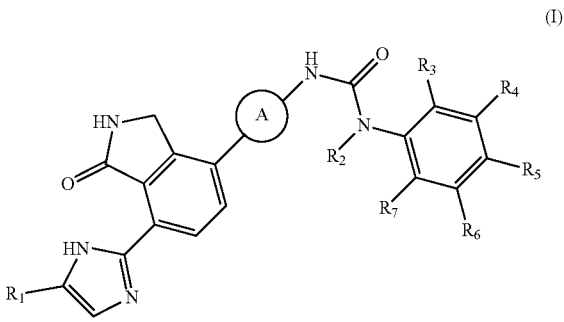

wherein,
A is

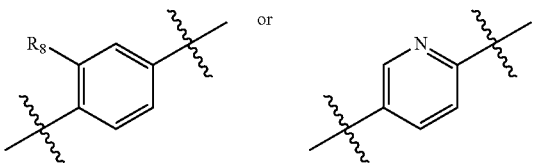

and $R_8$ is hydrogen, halogen, or $C_{1-3}$alkyl, $R_1$ and $R_2$ are each independently hydrogen or $C_{1-3}$alkyl,
$R_3$ to $R_7$ are each independently hydrogen, halogen, cyano, nitro or $C_{1-3}$haloalkyl.

In accordance with another aspect of the present invention, there is provided a pharmaceutical composition comprising same as an active ingredient for the treatment, relief or prevention of diseases caused by abnormal or uncontrolled activation of protein kinase.

DETAILED DESCRIPTION OF THE INVENTION

Embodiments of the present invention are explained in detail hereinafter.

In the present invention, there is provided a compound selected from the group consisting of a compound of formula (I) below and pharmaceutically acceptable salts, esters, prodrugs, hydrates, solvates and isomers thereof:

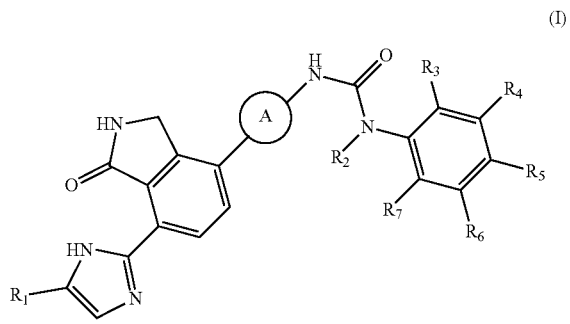

(I)

wherein,
A is

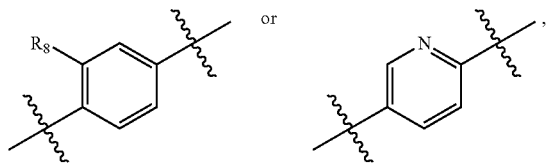

and $R_8$ is hydrogen, halogen, or $C_{1-3}$alkyl, $R_1$ and $R_2$ are each independently hydrogen or $C_{1-3}$alkyl, $R_3$ to $R_7$ are each independently hydrogen or electron withdrawing substituent, wherein the electron withdrawing substituent is, for example, halogen, cyano, nitro or $C_{1-3}$haloalkyl.

In one specific embodiment, said $R_3$ to $R_7$ are each independently hydrogen, fluoro, chloro, bromo, iodo, cyano, nitro, difluoromethyl or trifluoromethyl.

In another specific embodiment, said $R_1$ and $R_2$ are each independently hydrogen or methyl;

$R_3$ to $R_7$ are each independently hydrogen, fluoro, chloro, cyano or trifluoromethyl;

$R_8$ is hydrogen or fluoro.

The term "halo" or "halogen" as used herein refers to fluorine, chlorine, bromine or iodine, unless otherwise indicated.

The term "alkyl" as used herein refers to linear or branched hydrocarbon residues, unless otherwise indicated.

The compound of formula (I) according to the present invention may form a pharmaceutically acceptable salt derived from inorganic or organic acid, and such salt may be pharmaceutically acceptable nontoxic acid addition salt containing anion. For example, the salt may include acid addition salts formed by inorganic acids such as hydrochloric acid, sulfuric acid, nitric acid, phosphoric acid, hydrobromic acid, hydroiodic acid, and the like; organic carbonic acids such as tartaric acid, formic acid, citric acid, acetic acid, trichloroacetic acid, trifluoroacetic acid, gluconic acid, benzoic acid, lactic acid, fumaric acid, maleic acid, and the like; and sulfonic acids such as methanesulfonic acid, benzenesulfonic acid, p-toluenesulfonic acid, naphthalensulfonic acid, and the like. Among them, acid addition salts formed by sulfuric acid, methanesulfonic acid or hydrohalogenic acid and the like are preferred.

The "pharmaceutically acceptable salt" of the compound of formula (I) may be prepared by conventional methods well-known in the art. Specifically, the "pharmaceutically acceptable salt" in accordance of the present invention may be prepared by, e.g., dissolving the compound of formula (I) in a water-miscible organic solvent such as acetone, methanol, ethanol or acetonitrile and the like; adding an excessive amount of organic acid or an aqueous solution of inorganic acid thereto; precipitating or crystallizing the mixture thus obtained. Further, it may be prepared by further evaporating the solvent or excessive acid therefrom; and then drying the mixture or filtering the extract by using a suction filter.

The term "ester" as used herein refers to a chemical moiety having chemical structure of —(R)n-COOR', wherein R and R' are each independently selected from the group consisting of alkyl, cycloalkyl, aryl, heteroaryl (connected to oxygen atom by aromatic ring) and heteroalicyclic (connected by aromatic ring), and n is 0 or 1, unless otherwise indicated.

The term "prodrug" as used herein refers to a precursor compound that will undergo metabolic activation in vivo to produce the parent drug. Prodrugs are often useful because they can be easily administered as compared to parent drugs thereof in some cases. For instance, some prodrugs are bioavailable via oral administration unlike parent drugs thereof often show poor bioavailability. Further, the prodrugs may show improved solubility in the pharmaceutical composition as compared to parent drugs thereof. For instance, the compound of formula (I) may be administered in the form of an ester prodrug so as to increase drug delivery efficiency since the solubility of a drug can adversely affect the permeability across the cell membrane. Then, once the compound in the form of the ester prodrug enters a target cell, it may be metabolically hydrolyzed into a carboxylic acid and an active entity.

Hydrates or solvates of the compound of formula (I) are included within the scope of the present invention.

Further, the compound of formula (I) of the present invention can have an asymmetric carbon center, and thus may be present in the form of isomer including enantiomer, diastereomer or racemic mixture, such entire stereoisomers and mixtures being included within the scope of the present invention.

Particular examples of the compound of formula (I) of the present invention are as follow:

1) 1-(2,6-dichloro-phenyl)-3-{3-fluoro-4-[7-(5-methyl-1H-imidazol-2-yl)-1-oxo-2,3-dihydro-1H-isoindol-4-yl]-phenyl}-urea;
2) 1-{3-fluoro-4-[7-(5-methyl-1H-imidazol-2-yl)-1-oxo-2,3-dihydro-1H-isoindol-4-yl]-phenyl}-3-(2-trifluoromethyl-phenyl)-urea;
3) 1-(2,6-difluoro-phenyl)-3-{3-fluoro-4-[7-(5-methyl-1H-imidazol-2-yl)-1-oxo-2,3-dihydro-1H-isoindol-4-yl]-phenyl}-urea;
4) 1-(2-chloro-6-fluoro-phenyl)-3-{3-fluoro-4-[7-(5-methyl-1H-imidazol-2-yl)-1-oxo-2,3-dihydro-1H-isoindol-4-yl]-phenyl}-urea;
5) 1-(2,6-bis-trifluoromethyl-phenyl)-3-{3-fluoro-4-[7-(5-methyl-1H-imidazol-2-yl)-1-oxo-2,3-dihydro-1H-isoindol-4-yl]-phenyl}-urea;

6) 1-{3-fluoro-4-[7-(5-methyl-1H-imidazol-2-yl)-1-oxo-2,3-dihydro-1H-isoindol-4-yl]-phenyl}-3-(2-fluoro-6-trifluoromethyl-phenyl)-urea;
7) 1-{3-fluoro-4-[7-(5-methyl-TH-imidazol-2-yl)-1-oxo-2,3-dihydro-TH-isoindol-4-yl]-phenyl}-3-(2,4,6-trifluorophenyl)-urea;
8) 1-(2,6-difluoro-phenyl)-3-{3-fluoro-4-[7-(5-methyl-1H-imidazol-2-yl)-1-oxo-2,3-dihydro-TH-isoindol-4-yl]-phenyl}-1-methyl-urea;
9) 1-{3-fluoro-4-[7-(5-methyl-TH-imidazol-2-yl)-1-oxo-2,3-dihydro-TH-isoindol-4-yl]-phenyl}-3-pentafluorophenyl-urea;
10) 1-(2,5-difluorophenyl)-3-(3-fluoro-4-(7-(5-methyl-TH-imidazol-2-yl)-1-oxoisoindolin-4-yl)phenyl)urea;
11) 1-(2,4-difluoro-phenyl)-3-{3-fluoro-4-[7-(5-methyl-H-imidazol-2-yl)-1-oxo-2,3-dihydro-1H-isoindol-4-yl]-phenyl}-urea;
12) 1-{3-fluoro-4-[7-(5-methyl-TH-imidazol-2-yl)-1-oxo-2,3-dihydro-TH-isoindol-4-yl]-phenyl}-3-(2,3,6-trifluorophenyl)-urea;
13) 1-(3,5-difluoro-phenyl)-3-{3-fluoro-4-[7-(5-methyl-1H-imidazol-2-yl)-1-oxo-2,3-dihydro-1H-isoindol-4-yl]-phenyl}-urea;
14) 1-(3,4-difluoro-phenyl)-3-{3-fluoro-4-[7-(5-methyl-1H-imidazol-2-yl)-1-oxo-2,3-dihydro-1H-isoindol-4-yl]-phenyl}-urea;
15) 1-(4-cyano-3-fluorophenyl)-3-(3-fluoro-4-(7-(5-methyl-1H-imidazol-2-yl)-1-oxoisoindolin-4-yl)phenyl)urea;
16) 1-(4-chloro-3-(trifluoromethyl)phenyl)-3-(3-fluoro-4-(7-(5-methyl-1H-imidazol-2-yl)-1-oxoisoindolin-4-yl)phenyl)urea;
17) 1-(3-chloro-2,6-difluorophenyl)-3-(3-fluoro-4-(7-(5-methyl-1H-imidazol-2-yl)-1-oxoisoindolin-4-yl)phenyl)urea;
18) 1-(2-chloro-3,6-difluorophenyl)-3-(3-fluoro-4-(7-(5-methyl-1H-imidazol-2-yl)-1-oxoisoindolin-4-yl)phenyl)urea;
19) 1-(4-chloro-2,6-difluoro-phenyl)-3-{3-fluoro-4-[7-(5-methyl-1H-imidazol-2-yl)-1-oxo-2,3-dihydro-TH-isoindol-4-yl]-phenyl}-urea; and
20) 1-{3-fluoro-4-[7-(5-methyl-1H-imidazol-2-yl)-1-oxo-2,3-dihydro-TH-isoindol-4-yl]-phenyl}-3-(2,3,5,6-tetrafluoro-phenyl)-urea.

The compound selected from the group consisting of the compound of formula (I), pharmaceutically acceptable salts, esters, prodrugs, hydrates, solvates and isomers thereof may be used for the treatment, relief or prevention of diseases caused by abnormal or uncontrolled activation of protein kinase such as ABL (Abelson tyrosine kinase), ACK (Activated cdc42-associated kinase), AXL, Aurora, BLK (B lymphoid tyrosine kinase), BMX (Bone marrow X-linked kinase), BTK (Bruton's tyrosine kinase), CDK (Cyclin-dependent kinase), CSK (C-Src kinase), DDR (Discoidin domain receptor), EPHA (Ephrin type A receptor kinase), FER (Fer (fps/fes related) tyrosine kinase), FES (Feline sarcoma oncogene), FGFR (Fibroblast growth factor receptor), FGR, FLT (Fms-like tyrosine kinase), FRK (Fyn-related kinase), FYN, HCK (Hemopoietic cell kinase), IRR (Insulin-receptor-related-receptor), ITK (Interleukin 2-inducible T cell kinase), JAK (Janus kinase), KDR (Kinase insert domain receptor), KIT, LCK (Lymphocyte-specific protein tyrosine kinase), LYN, MAPK (Mitogen activated protein kinase), MER (c-Mer proto-oncogene tyrosine kinase), MET, MINK (Misshapen-like kinase), MNK (MAPK-interacting kinase), MST (Mammalian sterile 20-like kinase), MUSK (Muscle-specific kinase), PDGFR (Platelet-derived growth factor receptor), PLK (Polo-like kinase), RET (Rearranged during transfection), RON, SRC (Steroid receptor coactivator), SRM (Spermidine synthase), TIE (Tyrosine kinase with immunoglobulin and EGF repeats), SYK (Spleen tyrosine kinase), TNK1 (Tyrosine kinase, non-receptor, 1), TRK (Tropomyosin-receptor-kinase), TNIK (TRAF2 and NCK interacting kinase) and the like.

Accordingly, the present invention provides a use of the compound of formula (I), pharmaceutically acceptable salts, esters, prodrugs, hydrates, solvates and isomers thereof for the treatment, relief or prevention of diseases caused by abnormal or uncontrolled activation of protein kinase, and a use of the compound for the manufacture of a medicament for the treatment, relief or prevention of the diseases.

Further, the present invention provides a method for the treatment, relief or prevention of diseases caused by abnormal or uncontrolled activation of protein kinase in a mammal, comprising administering to the mammal a pharmaceutical composition comprising the compound of formula (I), pharmaceutically acceptable salts, esters, prodrugs, hydrates, solvates and isomers thereof.

Furthermore, the present invention provides a pharmaceutical composition for the treatment, relief or prevention of diseases caused by abnormal or uncontrolled activation of protein kinase in a mammal, comprising the compound of formula (I), pharmaceutically acceptable salts, esters, prodrugs, hydrates, solvates and isomers thereof.

The said diseases related with kinase activity may include any disease caused by abnormal or uncontrolled activation of protein kinase. Specific examples thereof may be cancer, inflammation associated with rheumatoid arthritis and osteoarthritis, asthma, allergy, atopic dermatitis, or psoriasis, but not limited hereto.

Examples of said cancer include lymphoma, leukemia, blood cancer, stomach cancer, non-small cell lung cancer, liver cancer, colorectal cancer, small bowel cancer, pancreatic cancer, brain cancer, bone cancer, melanoma, breast cancer, sclerosing adenosis, uterine cancer, cervical cancer, ovarian cancer, head and neck cancer, esophageal cancer, thyroid cancer, parathyroid cancer, kidney cancer, sarcoma, prostate cancer, urethral cancer, bladder cancer, fibroadenoma, or glioblastoma, but not limited hereto.

The pharmaceutical composition may further comprise at least one additive selected from the group consisting of antibiotic, alkylating agent, antimetabolite, hormonal agent, immunological agent, interferon-type agent and anticancer agent.

The pharmaceutical composition of the present invention may be formulated directly, or further contain conventional non-toxic pharmaceutically acceptable additives, e.g., a carrier and an excipient, to be formulated in accordance with any of the conventional methods well-known in the art.

The method for the treatment, relief or prevention may include, e.g., administering an effective amount of the pharmaceutical composition comprising the compound of the present invention to a subject suffering from, or at risk of, chronic renal failure, diabetes, cancer, AIDS, radiation therapy, chemotherapy, kidney dialysis or anemia caused by surgery. In one embodiment, the subject is preferably mammal, and more preferably, human.

The effective amount of the pharmaceutical composition of the present invention may be determined by conducting an ordinary test in order to find out the most effective administration route and suitable preparation method. The pharmaceutical composition of the present invention may be prepared into any type of formulation and drug delivery system by using any of the conventional methods well-known in the art. The inventive pharmaceutical composition may be formulated into injectable formulations, which may be administered by routes including intrathecal, intraventricular, intravenous, intraperitoneal, intranasal, intraocular, intramuscular, subcutaneous or intraosseous. Also, it may also be administered orally, or parenterally through the rectum, the intestines or the mucous membrane in the nasal cavity (see Gennaro, A. R., ed. (1995) Remington's Pharmaceutical Sciences). Preferably, the composition is administered topically, instead of enterally. For instance, the composition may be injected, or delivered via a targeted drug delivery system such as a reservoir formulation or a sustained release formulation.

The pharmaceutical formulation of the present invention may be prepared by any well-known methods in the art, such as mixing, dissolving, granulating, dragee-making, levigating, emulsifying, encapsulating, entrapping, or lyophilizing processes. As mentioned above, the compositions of the present invention may include one or more physiologically acceptable carriers such as excipients and adjuvants that facilitate processing of active molecules into preparations for pharmaceutical use.

Proper formulation is dependent upon the route of administration chosen. For injection, for example, the composition may be formulated in an aqueous solution, preferably in physiologically compatible buffers such as Hank's solution, Ringer's solution, or physiological saline buffer. For transmucosal or nasal administration, penetrants appropriate to the barrier to be permeated are used in the formulation. Such penetrants are generally known in the art. Ina preferred embodiment of the present invention, the inventive compound may be prepared in an oral formulation. For oral administration, the compounds can be formulated readily by combining the active compounds with pharmaceutically acceptable carriers known in the art. Such carriers enable the inventive compounds to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use may be obtained as solid excipients, optionally grinding a resulting mixture, and processing the mixture of granules, after adding suitable adjuvants, if desired, to obtain tablets or dragee cores. Suitable excipients may be, in particular, fillers such as sugars, including lactose, sucrose, mannitol, or sorbitol; cellulose formulation such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP) formulation. Also, disintegrating agents may be employed, such as cross-linked polyvinylpyrrolidone, agar, or alginic acid or a salt thereof such as sodium alginate. Also, wetting agents, such as sodium dodecyl sulfate and the like, may be added.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds doses.

Pharmaceutical formulations for oral administration may include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the compounds of the present invention may be administered transdermally, such as through a skin patch, or topically. In one aspect, the transdermal or topical formulations of the present invention can additionally comprise one or multiple penetration enhancers or other effectors, including agents that enhance migration of the delivered compound. Preferably, transdermal or topical administration may be used, e.g., in situations in which location specific delivery is desired.

For administration by inhalation, the compounds of the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, e.g., gelatin, for use in an inhaler or insufflators may be formulated. These typically contain a powder mix of the compound and a suitable powder base such as lactose or starch. Compositions formulated for parenteral administration by injection, e.g., by bolus injection or continuous infusion, can be presented in unit dosage form e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles may include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a reservoir formulation. Such long acting formulations may be administered by implantation (e.g., subcutaneous or intramuscular) or by intramuscular injection. Thus, for example, the inventive compounds may be formulated with suitable polymeric or hydrophobic materials (e.g., an emulsion in an acceptable oil) or ion exchange resins, or as sparingly soluble derivatives, e.g., a sparingly soluble salt.

For any composition used in the present methods of treatment, a therapeutically effective dose can be estimated initially using a variety of techniques well-known in the art. For example, based on information obtained from a cell culture assay, a dose can be formulated in animal models to achieve a circulating concentration range that includes the $IC_{50}$. Similarly, dosage ranges appropriate for human subjects can be determined, for example, using data obtained from cell culture assays and other animal studies.

A therapeutically effective dose of an agent refers to the amount of the agent that results in amelioration of symptoms or a prolongation of survival in a subject. Toxicity and therapeutic efficacy of such molecules can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods well-known in the art, in view of the specifics of a subject's condition.

In addition, the amount of agent or composition administered will be dependent on a variety of factors, including the age, weight, sex, health condition, degree of disease of the subject being treated, the severity of the affliction, the manner of administration, and the judgment of the prescribing physician.

Hereinafter, an exemplary method for preparing the compound of the present invention is explained.

Various starting materials may be prepared in accordance with conventional synthetic methods well-known in the art. Some of the starting materials are commercially available from manufacturers and suppliers of reagents, such as Aldrich, Sigma, TCI, Wako, Kanto, Fluorchem, Acros, Abocado, Alfa, Fluka, etc., but not limited thereto.

The compounds of the present invention can be prepared from readily available starting materials by conventional methods and processes below. Different methods may also be used for manufacturing the inventive compounds, unless otherwise specified as typical or preferred process conditions (i.e., reaction temperature, time, molar ratio of reactants, solvents, pressures, etc.). The optimal reaction conditions may vary depending on the particular reactants or solvents employed. Such conditions, however, can be determined by the skilled in the art by conventional optimization process.

In addition, those of ordinary skill in the art recognize that some functional groups can be protected/deprotected using various protecting groups before a certain reaction takes place. Suitable conditions for protecting and/or deprotecting specific functional group, and the use of protecting groups are well-known in the art.

For example, various kinds of protecting groups are described in T. W. Greene and G. M. Wuts, Protecting Groups in Organic Synthesis, Second edition, Wiley, New York, 1991, and other references cited above.

In one embodiment of the present invention, the compound of formula (I) of the present invention may be prepared by synthesizing an intermediate, Compound D, according to the Reaction Scheme 1 as shown below, and then subjecting Compound D through the procedure of Reaction Scheme 2 or 3. However, the method for synthesizing Compound D above is not limited to Reaction Scheme 1.

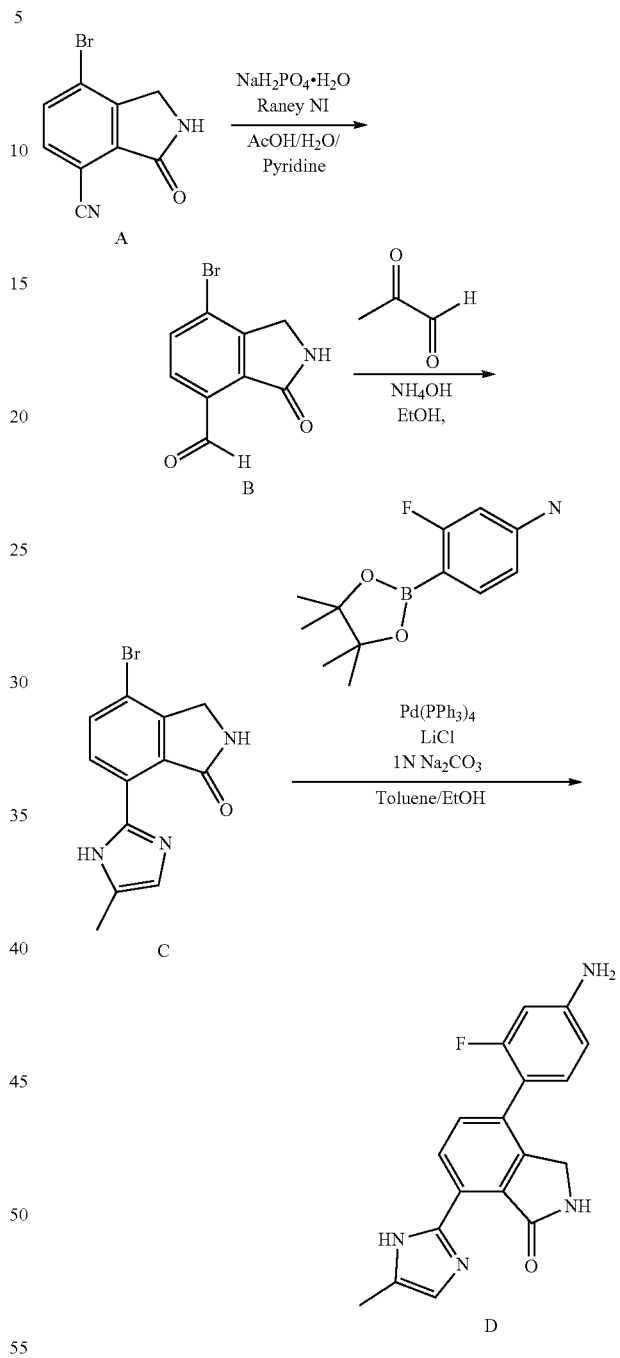

The method for preparing the starting material of Reaction Scheme 1, i.e., Compound A, is described in International Patent Publication WO2012/014017, and Compound D is prepared by the following methods.

<1-1> Synthesis of Compound B

Compound A (40 g, 168 mmol) was dispersed in acetic acid (400 mL), added with water (400 mL) and pyridine (800 mL), and then the temperature of the mixture thus formed was lowered to 10° C. The mixture was added with sodium phosphate monobasic monohydrate (280 g, 2.01 mol), and then further added with Raney Ni (101 g) in water (70 mL) to form a reaction solution. The reaction solution was heated to 50° C., allowed to react for 2 hours. Upon the completion of the reaction, the solution was cooled and filtered. The solution was washed with ethyl acetate (EA, 2.5 L), and the filtrate was added with water (800 mL) for extraction. An organic layer thus formed was separated, and concentrated under reduced pressure. Cooled water (800 mL) was added thereto, and a solid thus obtained was filtered and dried to obtain Compound B (26.7 g, yield: 66%).

$^1$H-NMR Spectrum (300 MHz, DMSO-$d_6$): 11.10 (s, 1H), 9.15 (s, 1H), 7.95 (d, J=8.1 Hz, 1H), 7.78 (d, J=8.1 Hz, 1H), 4.41 (s, 2H)

LCMS [M+1]: 241.1

<1-2> Synthesis of Compound C

Compound B (26.7 g, 111 mmol) was dispersed in ethanol (800 mL), and aqueous solutions of 48% methyl glyoxal (67 mL) and 28% ammonia (75 mL) were added thereto. The reaction solution thus formed was heated to 90° C., and stirred for 3 hours. Upon the completion of the reaction, the solution was concentrated under reduced pressure to reduce the volume of the reaction solution to about 200 mL, and a solid thus formed was filtered. The solid was washed with ethanol (50 mL) to obtain Compound C (17.2 g, yield: 53%).

$^1$H-NMR Spectrum (300 MHz, DMSO-$d_6$): 14.21-14.12 (m, 1H), 9.48 (s, 1H), 8.27 (d, J=8.4 Hz, 1H), 7.83 (d, J=8.4 Hz, 1H), 7.07-6.82 (m, 1H), 4.39 (s, 2H), 2.27-2.18 (m, 3H)

LCMS [M+1]: 293.1

<1-3> Synthesis of Compound D

Compound C (17.2 g, 58.9 mmol), 3-fluoro-4-(4,4,5,5-tetramethyl-[1,3,2]dioxaborolan-2-yl)-phenylamine (19.5 g, 82 mmol), LiCl (6.9 g, 165 mmol) and Pd(PPh$_3$)$_4$ (6.8 g, 5.9 mmol) were dispersed in a mixed solution of toluene (589 mL) and ethanol (589 mL), added with an aqueous solution of 1 N Na$_2$CO$_3$ (117 mL), and allowed to react at 85° C. for 12 hours. Upon completion of the reaction, the reaction solution was completely concentrated under reduced pressure. A mixed solution of acetone (1.2 L) and acetonitrile (1.2 L) was added thereto, and the reaction solution was stirred for 2 hours at 80° C., cooled, filtered and then washed with acetonitrile (0.5 L). The filtered solution was concentrated under reduced pressure to reduce the volume of the reaction solution to about 150 mL, and then filtered. A solid thus obtained was washed under reduced pressure with acetonitrile (60 mL), n-hexane (100 mL), and water (100 mL), respectively, and dried to yield Compound D, 4-(4-amino-2-fluorophenyl)-7-(5-methyl-1H-imidazol-2-yl)isoindolin-1-one (13.31 g, yield: 70%).

$^1$H-NMR Spectrum (300 MHz, DMSO-$d_6$): 14.44-14.34 (m, 1H), 9.36 (s, 1H), 8.36 (d, J=8.4 Hz, 1H), 7.51 (d, J=7.8 Hz, 1H), 7.16 (t, J=8.7 Hz, 1H), 7.04-6.79 (m, 1H), 6.49-6.42 (m, 2H), 5.65 (s, 2H), 4.36 (s, 2H), 2.28-2.18 (m, 3H)

LCMS [M+1]: 323.3

In order to prepare various compounds which can be represented by formula (I) of the present invention, a method for synthesizing such compounds by using the intermediate Compound D is specifically described in Reaction Schemes 2 and 3 below. However, this is a representative example of preparing the compound of formula (I) using the intermediate Compound D, and therefore, the preparation method of the compound of formula (I) is not limited hereto.

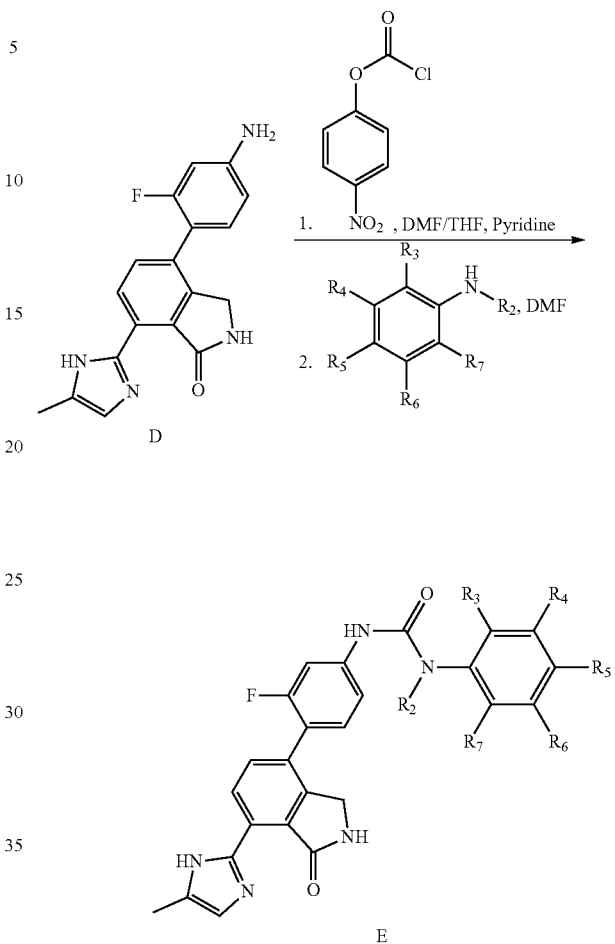

[Reaction Scheme 2]

Compound E disclosed in Reaction Scheme 2 was prepared by the following methods.

<2-1> Synthesis of Compound E According to Reaction Scheme 2

4-(4-amino-2-fluorophenyl)-7-(5-methyl-1H-imidazol-2-yl)isoindolin-1-one (Compound D, 1 equivalent) was dispersed in DMF/THF (1:4) to form a solution (0.08 in), and then pyridine (1.15 equivalent) and 4-nitrophenyl carbonochloridate (1.15 equivalent) were added thereto, followed by stirring for 4 hours. After the reaction had reached completion (TLC), n-hexane (same volume as THF, the reaction solution) was added thereto, followed by stirring for 30 minutes. A solid thus formed was washed with a mixed solvent of n-hexane:THF=1:1 (four times the volume of THF, reaction solution), filtered, and then dried. The dried compound was dispersed in DMF to form a solution (0.1 m), added with substituted phenylamine (6 to 15 equivalents), and then stirred for 20 minutes under microwave conditions (250 W, 250 psi, 150° C.). The reaction solution was diluted with ethyl acetate containing 5% methanol, and then washed with a saturated aqueous solution of NaHCO$_3$ and water. The organic layer was dried over anhydrous magnesium sulfate (MgSO$_4$), and then purified by silica gel column chromatography (eluent: methylene chloride:methanol=20:1) to obtain Compound E.

Compound E obtained in Reaction Scheme 2 may also be synthesized by Reaction Scheme 3 below.

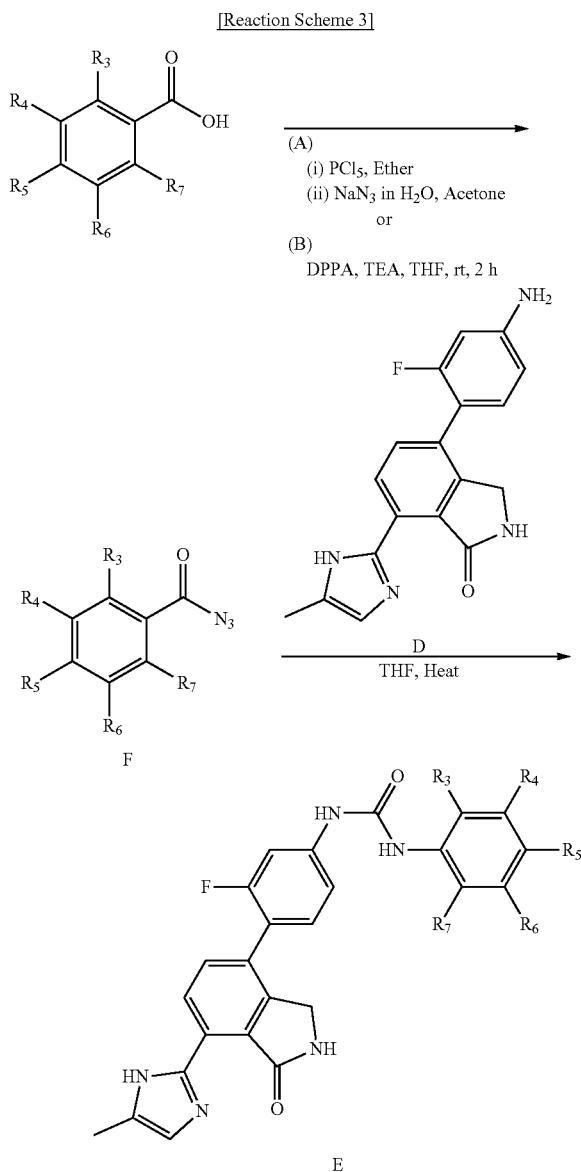

<3-1> (A) Synthesis of Compound E According to Reaction Scheme 3

Substituted benzoic acid (2 equivalents) was dispersed in diethyl ether to form a mixture (0.08 m), added with phosphorus pentachloride (PCl$_5$, 2.2 equivalents), and then stirred for 2 hours. Upon completion of the reaction, the organic solvent was concentrated under reduced pressure below room temperature, and then the reaction solution was diluted (0.08 m) by adding acetone to the reactant. Subsequently, sodium azide (NaN$_3$, 2.4 equivalents) in water (1/12 volume of acetone) was slowly added to the reaction solution dropwise at 0° C. After stirring for 2 hours at room temperature, the reactant was diluted with ethyl acetate, and then with water. The organic layer was dried over anhydrous magnesium sulfate (MgSO$_4$), dispersed in THF to form a solution (0.04 m), added with 4-(4-amino-2-fluorophenyl)-7-(5-methyl-1H-imidazol-2-yl)isoindolin-1-one (Compound D, 1 equivalent), and stirred for 4 hour at 90° C. Upon completion of the reaction, the solvent was concentrated under reduced pressure, and then purified by silica gel column chromatography (eluent: methylene chloride:methanol=20:1) to obtain Compound E.

Compound E synthesized in Reaction Scheme 2 above may also be synthesized by using another method according to Reaction Scheme 3.

<3-2> (B) Synthesis of Compound E According to Reaction Scheme 3

Substituted benzoic acid (2 equivalents) was dispersed in THF to form a solution (0.05 m), and then triethylamine (4 equivalents) and diphenylphosphorazidate (DPPA, 2.3 equivalents) were added thereto, followed by stirring for 2 hours at room temperature. The reaction solution was added with 4-(4-amino-2-fluorophenyl)-7-(5-methyl-1H-imidazol-2-yl)isoindolin-1-one (Compound D, 1 equivalent), and then stirred for 4 hours at 90° C. Subsequently, the reaction solution was diluted with ethyl acetate containing 5% methanol, and washed with water and a saturated aqueous solution of NaHCO$_3$. The organic layer was dried over anhydrous magnesium sulfate (MgSO$_4$), and then concentrated under reduced pressure. The concentrate thus obtained was purified by silica gel column chromatography (eluent: methylene chloride:methanol=20:1) to obtain Compound E.

Hereinafter, the present invention is described more specifically by the following Examples, but these are provided for illustration purposes only, and the present invention is not limited thereto.

Example 1: Preparation of 1-(2,6-dichloro-phenyl)-3-{3-fluoro-4-[7-(5-methyl-1H-imidazol-2-yl)-1-oxo-2,3-dihydro-1H-isoindol-4-yl]-phenyl}-urea 4-(4-amino-2-fluorophenyl)-7-(5-methyl-1H-imidazol-2-yl)isoindolin-1-one (Compound D, 0.1 g, 0.31 mmol) was dispersed in DMF (0.8 mL) and THF (3.4 mL), added with pyridine (0.03 mL) and 4-nitrophenyl carbonochloridate (0.07 g, 0.36 mmol), and then stirred for 4 hours. After confirming the completion of the reaction by TLC, n-hexane (3 mL) was added thereto, and stirred for 30 minutes. A solid thus formed was washed with a mixed solvent of n-hexane:THF=1:1 (12 mL), filtered and then dried. The dried compound was dispersed in DMF (3 mL), added with 2,6-dichloroaniline (0.34 g, 2.08 mmol), and then stirred for 20 minutes under microwave conditions (250 W, 250 psi, 150° C.). The reaction solution was diluted with ethyl acetate containing 5% methanol, and then washed sequentially with a saturated aqueous solution of NaHCO$_3$ and water. The organic layer was dried over anhydrous magnesium sulfate, concentrated, and then purified by silica gel column chromatography (eluent: methylene chloride:methanol=20:1) to obtain the title compound (0.03 g, yield: 19%).

$^1$H-NMR Spectrum (300 MHz, DMSO-d$_6$): 9.54 (s, 1H), 9.36 (s, 1H), 8.58 (s, 1H), 8.43 (d, J=8.1 Hz, 1H), 7.59 (m, 3H), 7.47 (t, J=8.4 Hz, 1H), 7.32 (m, 2H), 7.08 (s, 1H), 4.41 (s, 2H), 2.25 (m, 3H)

LCMS [M+1]: 511

Example 2: Preparation of 1-{3-fluoro-4-[7-(5-methyl-1H-imidazol-2-yl)-1-oxo-2,3-dihydro-1H-isoindol-4-yl]-phenyl}-3-(2-trifluoromethyl-phenyl)-urea 4-(4-amino-2-fluorophenyl)-7-(5-methyl-1H-imidazol-2-yl)isoindolin-1-one (Compound D, 0.1 g, 0.31 mmol) was dispersed in DMF (0.8 mL) and THF (3.4 mL), added with pyridine (0.03 mL) and 4-nitrophenyl carbonochloridate (0.07 g, 0.36 mmol), and then stirred for 4 hours. Subsequently, n-hexane (3 mL) was added to the mixture, and stirred for 30 minutes. A solid thus formed was washed with a mixed solution of n-hexane:THF=1:1 (12 mL), filtered and then dried. The dried compound was dispersed in DMF (2 mL), added with 2-trifluoromethyl aniline (0.74 g, 4.65 mmol), and then stirred for 3 hours at room temperature. The reaction solution was added sequentially with methanol (6 mL), and a saturated aqueous solution of $NaHCO_3$, and stirred for 30 minutes. A solid thus formed was filtered and washed with water. After drying the washed solid, the solid was purified by silica gel column chromatography (eluent: methylene chloride:methanol=20:1) to obtain the title compound (0.07 g, yield: 44%).

$^1$H-NMR Spectrum (300 MHz, DMSO-$d_6$): 9.54 (s, 1H), 9.36 (s, 1H), 8.58 (s, 1H), 8.43 (d, J=8.1 Hz, 1H), 7.59 (m, 3H), 7.47 (t, J=8.4 Hz, 1H), 7.32 (m, 2H), 7.08 (s, 1H), 4.41 (s, 2H), 2.25 (m, 3H)

LCMS [M+1]: 510.0

Example 3: Preparation of 1-(2,6-difluoro-phenyl)-3-{3-fluoro-4-[7-(5-methyl-1H-imidazol-2-yl)-1-oxo-2,3-dihydro-1H-isoindol-4-yl]-phenyl}-urea 2,6-difluoro-benzoic acid (0.04 g, 0.248 mmol) was dispersed in diethyl ether (3 mL), slowly added with phosphorus pentachloride ($PCl_5$, 0.057 g, 0.273 mmol), and then stirred for 1 hour. Upon completion of the reaction, the organic solvent was concentrated under reduced pressure below room temperature, and then the reaction solution was diluted by adding acetone (2 mL). Subsequently, sodium azide ($NaN_3$, 0.019 g, 0.298 mmol) dissolved in water (0.2 mL) was slowly added to the reaction solution dropwise at 0° C. After stirring the reaction solution for 2 hours at room temperature, 2,6-difluoro-benzoyl azide thus formed was diluted with ethyl acetate, and then washed with water. The organic layer was dried over anhydrous magnesium sulfate, dispersed in THF (1 mL), added with THF (4 mL) containing 4-(4-amino-2-fluorophenyl)-7-(5-methyl-1H-imidazol-2-yl)isoindolin-1-one (Compound D, 0.04 g, 0.124 mmol), and then stirred for 4 hours at 90° C. Upon completion of the reaction, the solvent was concentrated under reduced pressure, and then purified by silica gel column chromatography (eluent: methylene chloride:methanol=20:1) to obtain the title compound (0.025 g, yield: 42%).

$^1$H-NMR Spectrum (300 MHz, DMSO-$d_6$): 14.45-14.36 (m, 1H), 9.40-9.36 (m, 2H), 8.42 (d, J=8.1 Hz, 1H), 8.33 (s, 1H), 7.62-7.57 (m, 2H), 7.48 (t, J=8.4 Hz, 1H), 7.37-7.26 (m, 2H), 7.20-6.82 (m, 3H), 4.40 (s, 2H), 2.29-2.19 (m, 3H)

LCMS [M+1]: 478.4

Example 4: Preparation of 1-(2-chloro-6-fluoro-phenyl)-3-{3-fluoro-4-[7-(5-methyl-1H-imidazol-2-yl)-1-oxo-2,3-dihydro-1H-isoindol-4-yl]-phenyl}-urea 2-chloro-6-fluorobenzoic acid (0.054 g, 0.31 mmol) was dispersed in diethyl ether (3 mL), slowly added with phosphorus pentachloride ($PCl_5$, 0.074 g, 0.357 mmol), and then stirred for 1 hour. Upon completion of the reaction, the organic solvent was concentrated under reduced pressure below room temperature, and then the reaction solution was diluted by adding acetone (2 mL). Subsequently, sodium azide ($NaN_3$, 0.024 g, 0.372 mmol) dissolved in water (0.2 mL) was slowly added to the reaction solution dropwise at 0° C. After stirring the reaction solution for 2 hours at room temperature, the reaction solution was diluted with ethyl acetate and washed with water. The organic layer was dried over anhydrous magnesium sulfate, dispersed in THF (1 mL), added with THF (4 mL) containing 4-(4-amino-2-fluorophenyl)-7-(5-methyl-1H-imidazol-2-yl)isoindolin-1-one (Compound D, 0.05 g, 0.155 mmol), and then stirred for 3 hours at 90° C. Upon completion of the reaction, the solvent was concentrated under reduced pressure, and then purified by silica gel column chromatography (eluent: methylene chloride:methanol=20:1) to obtain the title compound (0.029 g, yield 42%).

$^1$H-NMR Spectrum (300 MHz, DMSO-$d_6$): 14.45-14.35 (m, 1H), 9.40-9.35 (m, 2H), 8.42 (d, J=8.1 Hz, 1H), 8.33 (s, 1H), 7.63-7.58 (m, 2H), 7.47 (t, J=8.4 Hz, 1H), 7.41-7.26 (m, 4H), 7.07-6.82 (m, 1H), 4.40 (s, 2H), 2.30-2.20 (m, 3H)

LCMS [M+1]: 494.4

Example 5: Preparation of 1-(2,6-bis-trifluoromethyl-phenyl)-3-{3-fluoro-4-[7-(5-methyl-1H-imidazol-2-yl)-1-oxo-2,3-dihydro-1H-isoindol-4-yl]-phenyl}-urea 2,6-bis-trifluoromethylbenzoic acid (0.088 g, 0.31 mmol) was dispersed in diethyl ether (3 mL), slowly added with phosphorus pentachloride ($PCl_5$, 0.068 g, 0.326 mmol), and then stirred for 1 hour. Upon completion of the reaction, the organic solvent was concentrated under reduced pressure below room temperature, and then the reaction solution was diluted by adding acetone (2 mL). Subsequently, sodium azide ($NaN_3$, 0.024 g, 0.372 mmol) dissolved in water (0.2 mL) was slowly added to the reaction solution dropwise at 0° C. After stirring the reaction solution for 2 hours at room temperature, 2,6-bis-trifluoromethylbenzoyl azide thus formed was diluted with ethyl acetate, and then washed with water. The organic layer was dried over anhydrous magnesium sulfate, dispersed in THF (1 mL), added with THF (4 mL) containing 4-(4-amino-2-fluorophenyl)-7-(5-methyl-1H-imidazol-2-yl)isoindolin-1-one (Compound D, 0.05 g, 0.155 mmol), and then stirred for 3 hours at 90° C. Upon completion of the reaction, the solvent was concentrated under reduced pressure, and the purified by silica gel column chromatography (eluent: methylene chloride:methanol=20:1) to obtain the title compound (0.018 g, yield: 20%).

$^1$H-NMR Spectrum (300 MHz, DMSO-$d_6$): 8.40 (d, J=8.4 Hz, 1H), 8.09-8.06 (m, 2H), 7.76 (t, J=8.1 Hz, 1H), 7.63 (d, J=8.1 Hz, 1H), 7.54 (d, J=12.9 Hz, 1H), 7.38 (t, J=8.4 Hz, 1H), 7.24 (d/d, J=8.4 Hz, 1H), 6.94 (s, 1H), 4.43 (s, 2H), 2.33 (s, 3H)

LCMS [M+1]: 578.4

Example 6: Preparation of 1-{3-fluoro-4-[7-(5-methyl-1H-imidazol-2-yl)-1-oxo-2,3-dihydro-1H-isoindol-4-yl]-phenyl}-3-(2-fluoro-6-trifluoromethyl-phenyl)-urea 2-fluoro-6-trifluoromethylbenzoic acid (0.058 g, 0.279 mmol) was dispersed in diethyl ether (3 mL), slowly added with phosphorus pentachloride ($PCl_5$, 0.064 g, 0.307 mmol), and then stirred for 1 hour. Upon completion of the reaction, the organic solvent was concentrated under reduced pressure below room temperature, and then the reaction solution was diluted by adding acetone (2 mL). Subsequently, sodium azide ($NaN_3$, 0.024 g, 0.363 mmol) dissolved in water (0.2 mL) was slowly added to the reaction solution dropwise 0° C. After stirring the reaction solution for 2 hours at room temperature, the reaction solution was diluted with ethyl acetate, and then washed with water. The organic layer was dried over anhydrous magnesium sulfate, dispersed in THF (1 mL), and then introduced to a flask which contained 4-(4-amino-2-fluorophenyl)-7-(5-methyl-1H-imidazol-2-yl)isoindolin-1-one (Compound D, 0.045 g, 0.14 mmol) diluted in THF (4 mL), followed by stirring for 4 hours at 90° C. Upon completion of the reaction, the solvent was concentrated under reduced pressure, and then purified by silica gel column chromatography (methylene chloride:methanol=20:1) to obtain the title compound (0.023 g, yield: 32%).

$^1$H-NMR Spectrum (300 MHz, DMSO-$d_6$): 8.41-8.39 (m, 1H), 7.64-7.50 (m, 5H), 7.39 (t, J=8.4 Hz, 1H), 7.25 (m, J=8.4 Hz, 1H), 6.94 (s, 1H), 4.43 (s, 2H), 2.33 (s, 3H)

LCMS [M+1]: 528.4

Example 7: Preparation of 1-{3-fluoro-4-[7-(5-methyl-1H-imidazol-2-yl)-1-oxo-2,3-dihydro-1H-isoindol-4-yl]-phenyl}-3-(2,4,6-trifluoro-phenyl)-urea 2,4,6-trifluorobenzoic acid (0.08 g, 0.45 mmol) was dispersed in diethyl ether (5.7 mL), slowly added with phosphorus pentachloride (PCl$_5$, 0.11 g, 0.52 mmol), and then stirred for 1 hour. Upon completion of the reaction, the organic solvent was concentrated under reduced pressure below room temperature, and then the reaction solution was diluted by adding acetone (3.8 mL). Subsequently, sodium azide (NaN$_3$, 0.035 g, 0.545 mmol) dissolved in water (0.28 mL) was slowly added to the reaction solution dropwise at 0° C. After stirring for 2 hours at room temperature, 2,4,6-trifluorobenzoyl azide thus formed was diluted with ethyl acetate, and then washed with water. The organic layer was dried over anhydrous magnesium sulfate, dispersed in THF (2 mL), added with THF (7.5 mL) containing 4-(4-amino-2-fluorophenyl)-7-(5-methyl-1H-imidazol-2-yl)isoindolin-1-one (Compound D, 0.073 g, 0.23 mmol), and then stirred for 3 hours at 90° C. Upon completion of the reaction, the solvent was concentrated under reduced pressure, and then purified by silica gel column chromatography (eluent: methylene chloride:methanol=20:1) to obtain the title compound (0.026 g, yield: 23%).

$^1$H-NMR Spectrum (300 MHz, DMSO-$d_6$): 14.46-14.37 (m 1H), 9.47-9.45 (br m, 1H), 9.37 (s, 1H), 8.45 (d, J=1.8 Hz, 1H), 8.30-8.27 (br m, 1H), 7.63-7.46 (m, 3H), 7.31-7.26 (m, 3H), 7.09-6.84 (m, 1H), 4.42 (s, 2H), 2.31-2.21 (m, 3H)

LCMS [M+1]: 496.3

Example 8: Preparation of 1-(2,6-difluoro-phenyl)-3-{3-fluoro-4-[7-(5-methyl-1H-imidazol-2-yl)-1-oxo-2,3-dihydro-1H-isoindol-4-yl]-phenyl}-1-methyl-urea 4-(4-amino-2-fluorophenyl)-7-(5-methyl-1H-imidazol-2-yl)isoindolin-1-one (Compound D, 0.1 g, 0.31 mmol) was dispersed in a mixed solution of DMF (0.8 mL) and THF (4 mL), and then pyridine (0.05 ml) and 4-nitrophenyl carbonochloridate (0.07 g, 0.36 mmol) were added thereto, followed by stirring for 4 hours. Upon completion of the reaction, n-hexane (3 mL) was added to the resulting a mixture, followed by stirring for 30 minutes. A solid thus formed was washed with a mixed solvent of n-hexane:THF=1:1 (12 mL), filtered, and then dried. The dried compound was dispersed in DMF (4 mL), added with 2,6-difluoro-methylaniline (0.294 g, 2.05 mmol), and then stirred for 12 hours at 100° C. The reaction solution was cooled to room temperature, diluted with ethyl acetate containing 5% methanol, and washed with a saturated aqueous solution of NaHCO$_3$ and water. The organic layer was dried over anhydrous magnesium sulfate, filtered, and concentrated. Finally the organic layer was purified by silica gel column chromatography (eluent: methylene chloride:methanol=20:1) to obtain the title compound (0.018 g, yield: 18%).

$^1$H-NMR Spectrum (300 MHz, DMSO-$d_6$): 14.45-14.36 (m, 1H), 9.36 (s, 1H), 8.91 (s, 1H), 8.42 (d, J=8.1 Hz, 1H), 7.61-7.34 (m, 5H), 7.26-7.21 (m, 2H), 7.07-6.82 (m, 1H), 4.40 (s, 2H), 3.20 (s, 3H), 2.30-2.20 (m, 3H)

LCMS [M+1]: 492.4

Example 9: Preparation of 1-{3-fluoro-4-[7-(5-methyl-1H-imidazol-2-yl)-1-oxo-2,3-dihydro-1H-isoindol-4-yl]-phenyl}-3-pentafluorophenyl-urea Pentafluorobenzoic acid (0.066 g, 0.31 mmol) was dispersed in diethyl ether (3 mL), slowly added with phosphorus pentachloride (PCl$_5$, 0.071 g, 0.341 mmol), and then stirred for 40 minutes. Upon completion of the reaction, the organic solvent was concentrated under reduced pressure below room temperature, and then the reaction solution was diluted by adding acetone (3 mL). Subsequently, sodium azide (NaN$_3$, 0.026 g, 0.403 mmol) dissolved in water (0.2 mL) was slowly added to the reaction solution dropwise at 0° C. After stirring the reaction solution for 1 hour at room temperature, the reaction solution was diluted with ethyl acetate, and then washed with water. The organic layer was dried over anhydrous magnesium sulfate, dispersed in THF (1 mL), and then introduced to a flask which contained 4-(4-amino-2-fluorophenyl)-7-(5-methyl-1H-imidazol-2-yl)isoindolin-1-one (Compound D, 0.050 g, 0.155 mmol) diluted in THF (3 mL), followed by stirring for 3 hours at 90° C. Upon completion of the reaction, the solvent was concentrated under reduced pressure, and then purified by silica gel column chromatography (methylene chloride:methanol=20:1) to obtain the title compound (0.023 g, yield: 28%).

$^1$H-NMR Spectrum (300 MHz, DMSO-$d_6$): 14.45-14.36 (m, 1H), 9.60 (s, 1H), 9.36 (s, 1H), 8.83 (br s, 1H), 8.43 (d, J=8.1 Hz, 1H), 7.62-7.57 (m, 2H), 7.50 (t, J=8.4 Hz, 1H), 7.30 (d, J=8.4 Hz, 1H), 7.08-6.83 (m, 1H), 4.40 (s, 2H), 2.30-2.20 (m, 3H)

LCMS [M+1]: 532.4

Example 10: Preparation of 1-(2,5-difluorophenyl)-3-(3-fluoro-4-(7-(5-methyl-1H-imidazol-2-yl)-1-oxoisoindolin-4-yl)phenyl)urea 2,5-difluorobenzoic acid (0.05 g, 0.32 mmol) was dispersed in THF (4 mL), and then triethylamine (0.088 mL, 0.63 mmol) and diphenylphosphorazidate (DPPA, 0.08 mL, 0.36 mmol) were added thereto, followed by stirring for 2 hours at room temperature. After checking that 2,5-difluorobenzoyl azide was formed, Compound D (0.051 g, 0.16 mmol) was added thereto, followed by stirring for 4 hours at 90° C. Upon completion of the reaction, the reaction solution was diluted with ethyl acetate containing 5% methanol, and then washed with a saturated aqueous solution of NaHCO$_3$. Subsequently, the organic layer was dried over anhydrous magnesium sulfate, and then concentrated under reduced pressure. The concentrate thus obtained was purified by silica gel column chromatography (eluent: methylene chloride:methanol=20:1) to obtain the title compound (0.026 g, yield: 34%).

$^1$H-NMR Spectrum (300 MHz, DMSO-$d_6$): 14.47-14.37 (m, 1H), 9.58 (s, 1H), 9.37 (s, 1H), 8.96 (s, 1H), 8.45 (d, J=8.4 Hz, 1H), 8.06-7.99 (m, 1H), 7.67-7.49 (m, 3H), 7.36-7.09 (m, 2H), 6.89-6.84 (m, 1H), 4.43 (s, 2H), 2.31-2.22 (m, 3H)

LCMS [M+1]: 478.4

Example 11: Preparation of 1-(2,4-difluoro-phenyl)-3-{3-fluoro-4-[7-(5-methyl-1H-imidazol-2-yl)-1-oxo-2,3-dihydro-1H-isoindol-4-yl]-phenyl}-urea 2,4-difluorobenzoic acid (0.04 g, 0.248 mmol) was dispersed in THF (3 mL), and then triethylamine (0.069 mL, 0.496 mmol) and diphenylphosphorazidate (DPPA, 0.075 g, 0.273 mmol) were added thereto, followed by stirring for 2 hours at room temperature. 4-(4-amino-2-fluorophenyl)-7-(5-methyl-1H-imidazol-2-yl)isoindolin-1-one (Compound D, 0.040 g, 0.124 mmol) was added to the mixture, followed by stirring for 4 hours at 90° C. Upon completion of the reaction, the reaction solution was diluted with ethyl acetate containing 5% methanol, and then washed with water and a saturated aqueous solution of NaHCO₃. Subsequently, the organic layer was dried over anhydrous magnesium sulfate, and then concentrated under reduced pressure. The concentrate thus obtained was purified by silica gel column chromatography (eluent: methylene chloride:methanol=20:1) to obtain the title compound (0.024 g, yield: 42%).

¹H-NMR Spectrum (300 MHz, DMSO-d₆): 14.45-14.36 (m, 1H), 9.39-9.35 (m, 2H), 8.64 (s, 1H), 8.43 (d, J=8.1 Hz, 1H), 8.09-8.00 (m, 1H), 7.65-7.59 (m, 2H), 7.49 (t, J=8.4 Hz, 1H), 7.35-7.21 (m, 2H), 7.08-6.83 (m, 2H), 4.41 (s, 2H), 2.30-2.20 (m, 3H)

LCMS [M+1]: 478.4

Example 12: Preparation of 1-{3-fluoro-4-[7-(5-methyl-1H-imidazol-2-yl)-1-oxo-2,3-dihydro-1H-isoindol-4-yl]-phenyl}-3-(2,3,6-trifluoro-phenyl)-urea 2,3,6-trifluorobenzoic acid (0.044 g, 0.248 mmol) was dispersed in diethyl ether (4 mL), slowly added with phosphorus pentachloride (PCl₅, 0.057 g, 0.273 mmol), and then stirred for 40 minutes. Upon completion of the reaction, the organic solvent was concentrated under reduced pressure below room temperature, and then the reaction solution was diluted by adding acetone (3 mL). Subsequently, sodium azide (NaN₃, 0.021 g, 0.322 mmol) in water (0.2 mL) was slowly added to the reaction solution dropwise at 0° C. After stirring the reaction solution for 1 hour at room temperature, the reaction solution was diluted with ethyl acetate, and then washed with water. The organic layer was dried over anhydrous magnesium sulfate, dispersed in THF (1 mL), and then introduced to a flask which contained 4-(4-amino-2-fluorophenyl)-7-(5-methyl-1H-imidazol-2-yl)isoindolin-1-one (Compound D, 0.040 g, 0.124 mmol) diluted in THF (3 mL), followed by stirring for 6 hours at 90° C. Upon completion of the reaction, the solvent was concentrated under reduced pressure, and then purified by silica gel column chromatography (eluent: methylene chloride:methanol=20:1) to obtain the title compound (0.022 g, yield: 36%).

¹H-NMR Spectrum (300 MHz, DMSO-d₆): 14.45-14.35 (m, 1H), 9.51 (br s, 1H), 9.35 (s, 1H), 8.62 (br s, 1H), 8.43 (d, J=8.1 Hz, 1H), 7.62-7.57 (m, 2H), 7.48 (t, J=8.4 Hz, 1H), 7.44-7.34 (m, 1H), 7.31-7.20 (m, 2H), 7.07-6.83 (m, 1H), 4.40 (s, 2H), 2.30-2.20 (m, 3H)

LCMS [M+1]: 496.4

Example 13: Preparation of 1-(3,5-difluoro-phenyl)-3-{3-fluoro-4-[7-(5-methyl-1H-imidazol-2-yl)-1-oxo-2,3-dihydro-1H-isoindol-4-yl]-phenyl}-urea 3,5-difluorobenzoic acid (0.04 g, 0.248 mmol) was dispersed in THF (4 mL), and then triethylamine (0.069 mL, 0.496 mmol) and diphenylphosphorazidate (DPPA, 0.075 g, 0.273 mmol) were added thereto, followed by stirring for 1 hour at room temperature. 4-(4-amino-2-fluorophenyl)-7-(5-methyl-1H-imidazol-2-yl)isoindolin-1-one (Compound D, 0.040 g, 0.124 mmol) was added to the reaction solution, followed by stirring for 4 hours at 90° C. The reaction solution was cooled to room temperature, diluted with ethyl acetate, and then washed water and a saturated aqueous solution of NaHCO₃. The organic layer was dried over anhydrous magnesium sulfate, and then concentrated under reduced pressure. The concentrate thus obtained was purified by silica gel column chromatography (eluent: methylene chloride:methanol=20:1) to obtain the title compound (0.032 g, yield: 55%).

¹H-NMR Spectrum (300 MHz, DMSO-d₆): 14.45-14.36 (m, 1H), 9.50 (s, 2H), 9.36 (s, 1H), 8.43 (d, J=8.1 Hz, 1H), 7.64-7.60 (m, 2H), 7.50 (t, J=8.4 Hz, 1H), 7.30-7.20 (m, 3H), 7.08-6.77 (m, 2H), 4.41 (s, 2H), 2.30-2.20 (m, 3H)

LCMS [M+1]: 478.3

Example 14: Preparation of 1-(3,4-difluoro-phenyl)-3-{3-fluoro-4-[7-(5-methyl-1H-imidazol-2-yl)-1-oxo-2,3-dihydro-1H-isoindol-4-yl]-phenyl}-urea 3,4-difluorobenzoic acid (0.05 g, 0.32 mmol) was dispersed in THF (4 mL), and then triethylamine (0.088 mL, 0.63 mmol) and diphenylphosphorazidate (DPPA, 0.08 mL, 0.36 mmol) were added thereto, followed by stirring for 2 hours at room temperature. After checking that 3,4-difluorobenzoyl azide was formed, 4-(4-amino-2-fluorophenyl)-7-(5-methyl-1H-imidazol-2-yl)isoindolin-1-one (Compound D, 0.051 g, 0.16 mmol) was added thereto, followed by stirring for 4 hours at 90° C. Upon completion of the reaction, the reaction solution was diluted with ethyl acetate containing 5% methanol, and then washed with a saturated aqueous solution of NaHCO₃. Subsequently, the organic layer was dried over anhydrous magnesium sulfate, and then concentrated under reduced pressure. The concentrate thus obtained was purified by silica gel column chromatography (eluent: methylene chloride methanol=20:1) to obtain the title compound (0.035 g, yield: 46%).

¹H-NMR Spectrum (300 MHz, DMSO-d₆): 14.40 (br s, 1H), 9.37 (s, 1H), 9.13-9.03 (m, 2H), 8.44 (d, J=8.1 Hz, 1H), 7.71-7.47 (m, 4H), 7.41-7.27 (m, 3H), 7.18-7.16 (m, 1H), 7.00 (s, 1H), 4.43 (s, 2H), 2.26 (s, 3H)

LCMS [M+1]: 478.4

Example 15: Preparation of 1-(4-cyano-3-fluoro-phenyl)-3-(3-fluoro-4-(7-(5-methyl-1H-imidazol-2-yl)-1-oxoisoindolin-4-yl)phenyl)urea 4-cyano-3-fluorobenzoic acid (0.08 g, 0.48 mmol) was dispersed in THF (6.1 mL), added with triethylamine (0.14 mL, 0.97 mmol) and diphenylphosphorazidate (DPPA, 0.12 mL, 0.56 mmol), and then stirred for 2 hours at room temperature. After checking that 4-cyano-3-fluorobenzoyl azide was formed, 4-(4-amino-2-fluorophenyl)-7-(5-methyl-1H-imidazol-2-yl)isoindolin-1-one (Compound D, 0.078 g, 0.24 mmol) was added thereto, followed by stirring for 4 hours at 90° C. Upon completion of the reaction, the reaction solution was diluted with ethyl acetate containing 5% methanol, and then washed with a saturated aqueous solution of NaHCO$_3$. Subsequently, the organic layer was dried over anhydrous magnesium sulfate, and then concentrated under reduced pressure. The concentrate thus obtained was purified by silica gel column chromatography (eluent: methylene chloride:methanol=20:1) to obtain the title compound (0.012 g, yield: 10%).

$^1$H-NMR Spectrum (300 MHz, DMSO-d$_6$): 14.40 (br s, 1H), 9.89 (s, 1H), 9.64 (s, 1H), 9.37 (s, 1H), 8.44 (d, J=8.7 Hz, 1H), 7.94-7.15 (m, 7H), 7.01-6.99 (m, 1H), 4.43 (s, 2H), 2.26 (s, 3H)

LCMS [M+1]: 485.4

Example 16: Preparation of 1-(4-chloro-3-(trifluoromethyl)phenyl)-3-(3-fluoro-4-(7-(5-methyl-1H-imidazol-2-yl)-1-oxoisoindolin-4-yl)phenyl)urea 4-chloro-3-trifluoromethylbenzoic acid (0.08 g, 0.35 mmol) was dispersed in THF (4.5 mL), and then triethylamine (0.1 mL, 0.71 mmol) and diphenylphosphorazidate (DPPA, 0.09 mL, 0.41 mmol) were added thereto, followed by stirring for 2 hours at room temperature. After checking that 4-chloro-3-trifluoromethylbenzoyl azide was formed, 4-(4-amino-2-fluorophenyl)-7-(5-methyl-1H-imidazol-2-yl)isoindolin-1-one (Compound D, 0.057 g, 0.18 mmol) was added thereto, followed by stirring for 4 hours at 90° C. Upon completion of the reaction, the reaction solution was diluted with ethyl acetate containing 5% methanol, and then washed with a saturated aqueous solution of NaHCO$_3$. Subsequently, the organic layer was dried over anhydrous magnesium sulfate, and then concentrated under reduced pressure. The concentrate thus obtained was purified by silica gel column chromatography (eluent: methylene chloride:methanol=20:1) to obtain the title compound (0.012 g, yield: 12%).

$^1$H-NMR Spectrum (300 MHz, DMSO-d$_6$): 14.47-14.37 (m, 1H), 9.36-9.32 (m, 2H), 9.25 (s, 1H), 8.45 (d, J=8.1 Hz, 1H), 8.12-8.05 (m, 1H), 7.71-7.61 (m, 4H), 7.54-7.48 (m, 1H), 7.33-7.29 (m, 1H), 7.09-6.85 (m, 1H), 4.42 (s, 2H), 2.32-2.22 (m, 3H)

LCMS [M+1]: 544.3

Example 17: Preparation of 1-(3-chloro-2,6-difluorophenyl)-3-(3-fluoro-4-(7-(5-methyl-1H-imidazol-2-yl)-1-oxoisoindolin-4-yl)phenyl)urea 3-chloro-2,6-difluorobenzoic acid (0.08 g, 0.41 mmol) was dispersed in diethyl ether (5.2 mL), slowly added with phosphorus pentachloride (PCl$_5$, 0.099 g, 0.48 mmol), and then stirred for 1 hour. Upon completion of the reaction, the organic solvent was concentrated under reduced pressure below room temperature, and then the reaction solution was diluted by adding acetone (3.5 mL). Subsequently, sodium azide (NaN$_3$, 0.032 g, 0.50 mmol) dissolved in water (0.25 mL) was slowly added to the reaction solution dropwise at 0° C. After stirring the reaction solution for 2 hours at room temperature, 3-chloro-2,6-difluorobenzoyl azide thus formed was diluted with ethyl acetate, followed by washing with water. The organic layer was dried over anhydrous magnesium sulfate, dispersed in THF (1.6 mL), added with THF (1.6 mL) containing 4-(4-amino-2-fluorophenyl)-7-(5-methyl-1H-imidazol-2-yl)isoindolin-1-one (Compound D, 0.067 g, 0.21 mmol), and then stirred for 3 hours at 90° C. Upon completion of the reaction, the solvent was concentrated, and then purified by silica gel column chromatography (eluent: methylene chloride:methanol=20:1) to obtain the title compound (0.017 g, yield: 16%).

$^1$H-NMR Spectrum (300 MHz, DMSO-d$_6$): 14.47-14.38 (m, 1H), 9.49-9.39 (m, 2H), 8.53 (s, 1H), 8.44 (d, J=8.1 Hz, 1H), 7.63-7.47 (m, 4H), 7.31-7.24 (m, 2H), 7.09-6.84 (m, 1H), 4.42 (s, 2H), 2.31-2.21 (m, 3H)

LCMS [M+1]: 512.3

Example 18: Preparation of 1-(2-chloro-3,6-difluorophenyl)-3-(3-fluoro-4-(7-(5-methyl-1H-imidazol-2-yl)-1-oxoisoindolin-4-yl)phenyl)urea 2-chloro-3,6-difluorobenzoic acid (0.08 g, 0.41 mmol) was dispersed in diethyl ether (5.2 mL), slowly added with phosphorus pentachloride (PCl$_5$, 0.099 g, 0.48 mmol), and then stirred for 1 hour. Upon completion of the reaction, the organic solvent was concentrated under reduced pressure below room temperature, and then the reaction solution was diluted by adding acetone (3.5 mL). Subsequently, sodium azide (NaN$_3$, 0.032 g, 0.50 mmol) dissolved in water (0.25 mL) was slowly added to the reaction solution dropwise at 0° C. After stirring the reaction solution for 2 hours at room temperature, 2-chloro-3,6-difluorobenzoyl azide thus formed was diluted with ethyl acetate, followed by washing with water. The organic layer was dried over anhydrous magnesium sulfate, dispersed in THF (1.6 mL), added with THF (7 mL) containing 4-(4-amino-2-fluorophenyl)-7-(5-methyl-1H-imidazol-2-yl)isoindolin-1-one (Compound D, 0.067 g, 0.21 mmol), and then stirred for 3 hours at 90° C. Upon completion of the reaction, the solvent was concentrated under reduced pressure, and the purified by silica gel column chromatography (eluent: methylene chloride:methanol=20:1) to obtain the title compound (0.038 g, yield: 36%).

$^1$H-NMR Spectrum (300 MHz, DMSO-d$_6$): 14.46-14.37 (m, 1H), 9.51 (s, 1H), 9.37 (s, 1H), 8.58 (s, 1H), 8.44 (d, J=8.1 Hz, 1H), 7.63-7.59 (m, 2H), 7.52-7.29 (m, 4H), 7.09-6.84 (m, 1H), 4.42 (s, 2H), 2.31-2.21 (m, 3H)

LCMS [M+1]: 512.3

Example 19: Preparation of 1-(4-chloro-2,6-difluoro-phenyl)-3-{3-fluoro-4-[7-(5-methyl-1H-imidazol-2-yl)-1-oxo-2,3-dihydro-1H-isoindol-4-yl]-phenyl}-urea 4-chloro-2,6-difluorobenzoic acid (0.060 g, 0.31 mmol) was dispersed in diethyl ether (4 mL), slowly added with phosphorus pentachloride (PCl$_5$, 0.071 g, 0.341 mmol), and then stirred for 40 minutes. Upon completion of the reaction, the organic solvent was concentrated under reduced pressure below room temperature, and then the reaction solution was diluted by adding acetone (3 mL). Subsequently, sodium azide (NaN$_3$, 0.026 g, 0.403 mmol) dissolved in water (0.2 mL) was slowly added to the reaction solution dropwise at 0° C. After stirring the reaction solution for 1 hour at room temperature, the reaction solution was diluted with ethyl acetate, and then washed with water. The organic layer was dried over anhydrous magnesium sulfate, dispersed in THF (1 mL), and then introduced to a flask which contained 4-(4-amino-2-fluorophenyl)-7-(5-methyl-1H-imidazol-2-yl)isoindolin-1-one (Compound D, 0.050 g, 0.155 mmol) dissolved in THF (3 mL), followed by stirring for 4 hours at 90° C. Upon completion of the reaction, the solvent was concentrated under reduced pressure, and then purified by silica gel column chromatography (eluent: methylene chloride methanol=20:1) to obtain the title compound (0.024 g, yield: 30%).

$^1$H-NMR Spectrum (300 MHz, DMSO-d$_6$): 14.46-14.37 (m, 1H), 9.86 (s, 1H), 9.38 (s, 1H), 8.82 (s, 1H), 8.41 (d, J=8.1 Hz, 1H), 7.63-7.59 (m, 2H), 7.52-7.29 (m, 4H), 6.97 (s, 1H), 4.42 (s, 2H), 2.21 (s, 3H)

LCMS [M+1]: 512.3

Example 20: Preparation of 1-{3-fluoro-4-[7-(5-methyl-1H-imidazol-2-yl)-1-oxo-2,3-dihydro-1H-isoindol-4-yl]-phenyl}-3-(2,3,5,6-tetrafluoro-phenyl)-urea 2,3,5,6-tetrafluorobenzoic acid (0.08 g, 0.41 mmol) was diluted in diethyl ether (5.2 mL), slowly added with phosphorus pentachloride (PCl$_5$, 0.099 g, 0.48 mmol), and then stirred for 1 hour. Upon completion of the reaction, the organic solvent was concentrated under reduced pressure below room temperature, and then the reaction solution was diluted by adding acetone (3.4 mL). Subsequently, sodium azide (NaN$_3$, 0.032 g, 0.50 mmol) dissolved in water (0.25 mL) was slowly added to the reaction solution dropwise at 0° C. After stirring the reaction solution for 2 hours at room temperature, 2,3,5,6-tetrafluorobenzoyl azide thus formed was diluted with ethyl acetate, and then washed with water. The organic layer was dried over anhydrous magnesium sulfate, dispersed in THF (1.6 mL), added with THF (7 mL) containing 4-(4-amino-2-fluorophenyl)-7-(5-methyl-1H-imidazol-2-yl)isoindolin-1-one (Compound D, 0.066 g, 0.21 mmol), and then stirred for 3 hours at 90° C. Upon completion of the reaction, the solvent was concentrated under reduced pressure, and then purified by silica gel column chromatography (eluent: methylene chloride:methanol=20:1) to obtain the title compound (0.014 g, yield: 13%)

$^1$H-NMR Spectrum (300 MHz, DMSO-d$_6$): 8.45 (d, J=8.1 Hz, 1H), 7.69-7.61 (m, 2H), 7.48-7.33 (m, 3H), 7.00 (s, 1H), 4.48 (s, 2H), 2.38 (s, 3H)

LCMS [M+1]: 514.3

The compounds obtained in Examples 1 to 20 are represented by the following structural formula, as shown in Table 1 below.

TABLE 1

| Compound | Name | Formula |
|---|---|---|
| 1 | 1-(2,6-dichloro-phenyl)-3-{3-fluoro-4-[7-(5-methyl-1H-imidazol-2-yl)-1-oxo-2,3-dihydro-1H-isoindol-4-yl]-phenyl}-urea | |
| 2 | 1-{3-fluoro-4-[7-(5-methyl-1H-imidazol-2-yl)-1-oxo-2,3-dihydro-1H-isoindol-4-yl]-phenyl}-3-(2-trifluoromethyl-phenyl)-urea | |
| 3 | 1-(2,6-difluoro-phenyl)-3-{3-fluoro-4-[7-(5-methyl-1H-imidazol-2-yl)-1-oxo-2,3-dihydro-1H-isoindol-4-yl]-phenyl}-urea | |
| 4 | 1-(2-chloro-6-fluoro-phenyl)-3-{3-fluoro-4-[7-(5-methyl-1H-imidazol-2-yl)-1-oxo-2,3-dihydro-1H-isoindol-4-yl]-phenyl}-urea | |

TABLE 1-continued

| Compound | Name |
|---|---|
| 5 | 1-(2,6-bis-trifluoromethyl-phenyl)-3-{3-fluoro-4-[7-(5-methyl-1H-imidazol-2-yl)-1-oxo-2,3-dihydro-1H-isoindol-4-yl]-phenyl}-urea |
| 6 | 1-{3-fluoro-4-[7-(5-methyl-1H-imidazol-2-yl)-1-oxo-2,3-dihydro-1H-isoindol-4-yl]-phenyl}-3-(2-fluoro-6-trifluoromethyl-phenyl)-urea |
| 7 | 1-{3-fluoro-4-[7-(5-methyl-1H-imidazol-2-yl)-1-oxo-2,3-dihydro-1H-isoindol-4-yl]-phenyl}-3-(2,4,6-trifluoro-phenyl)-urea |
| 8 | 1-(2,6-difluoro-phenyl)-3-{3-fluoro-4-[7-(5-methyl-1H-imidazol-2-yl)-1-oxo-2,3-dihydro-1H-isoindol-4-yl]-phenyl}-1-methyl-urea |
| 9 | 1-{3-fluoro-4-[7-(5-methyl-1H-imidazol-2-yl)-1-oxo-2,3-dihydro-1H-isoindol-4-yl]-phenyl}-3-pentafluorophenyl-urea |

TABLE 1-continued

| Compound | Name | Formula |
|---|---|---|
| 10 | 1-(2,5-difluorophenyl)-3-(3-fluoro-4-(7-(5-methyl-1H-imidazol-2-yl)-1-oxoisoindolin-4-yl)phenyl)urea | |
| 11 | 1-(2,4-difluoro-phenyl)-3-{3-fluoro-4-[7-(5-methyl-1H-imidazol-2-yl)-1-oxo-2,3-dihydro-1H-isoindol-4-yl]-phenyl}-urea | |
| 12 | 1-{3-fluoro-4-[7-(5-methyl-1H-imidazol-2-yl)-1-oxo-2,3-dihydro-1H-isoindol-4-yl]-phenyl}-3-(2,3,6-trifluoro-phenyl)-urea | |
| 13 | 1-(3,5-difluoro-phenyl)-3-{3-fluoro-4-[7-(5-methyl-1H-imidazol-2-yl)-1-oxo-2,3-dihydro-1H-isoindol-4-yl]-phenyl}-urea | |
| 14 | 1-(3,4-difluoro-phenyl)-3-{3-fluoro-4-[7-(5-methyl-1H-imidazol-2-yl)-1-oxo-2,3-dihydro-1H-isoindol-4-yl]-phenyl}-urea | |
| 15 | 1-(4-cyano-3-fluorophenyl)-3-(3-fluoro-4-(7-(5-methyl-1H-imidazol-2-yl)-1-oxoisoindolin-4-yl)phenyl)urea | |

TABLE 1-continued

| Compound | Name | Formula |
|---|---|---|
| 16 | 1-(4-chloro-3-(trifluoromethyl)phenyl)-3-(3-fluoro-4-(7-(5-methyl-1H-imidazol-2-yl)-1-oxoisoindolin-4-yl)phenyl)urea | |
| 17 | 1-(3-chloro-2,6-difluorophenyl)-3-(3-fluoro-4-(7-(5-methyl-1H-imidazol-2-yl)-1-oxoisoindolin-4-yl)phenyl)urea | |
| 18 | 1-(2-chloro-3,6-difluorophenyl)-3-(3-fluoro-4-(7-(5-methyl-1H-imidazol-2-yl)-1-oxoisoindolin-4-yl)phenyl)urea | |
| 19 | 1-(4-chloro-2,6-difluoro-phenyl)-3-{3-fluoro-4-[7-(5-methyl-1H-imidazol-2-yl)-1-oxo-2,3-dihydro-1H-isoindol-4-yl]-phenyl}-urea | |
| 20 | 1-{3-fluoro-4-[7-(5-methyl-1H-imidazol-2-yl)-1-oxo-2,3-dihydro-1H-isoindol-4-yl]-phenyl}-3-(2,3,5,6-tetrafluoro-phenyl)-urea | |

The compounds prepared from Examples were tested for biological assays as follows.

Evaluation of biological activities of the compounds in accordance with the present invention may be conducted by any conventional methods known in the art. Appropriate test methods are well known in the art. The following tests are examples for assaying effects of the inventive compounds on various kinases, which are not limited hereto. The compounds of the present invention show their activities in at least one of the following assays.

Experimental Example 1: Assay for BTK Inhibition Activity (ELISA Method)

In order to evaluate the activity of the compounds of the present invention as a BTK inhibitor, commercially available BTK (Promega) was used for this experiment. Specifically, an enzymatic reaction was conducted by mixing 0.4 nM of BTK enzyme, 40 µM of biotin-S1 substrate peptide and 50 M of ATP in a reaction buffer (15 mM Tris-HCl (pH 7.5), 20 mM $MgCl_2$, 2 mM $MnCl_2$, 2 mM DTT, 0.1 mg/ml BSA). The mixture was treated with the test compounds at predetermined concentrations and allowed to react for 20 minutes at 30° C. Upon completion of the reaction, the activities of the test compounds were measured by ELISA method. The absorbance value of an untreated sample was used as a control (100% control). BTK enzyme activities were measured after treatment with various concentrations of the test compounds, and the concentration of test compounds resulting in 50% inhibition of BTK enzyme as compared to the control was determined as $IC_{50}$ of BTK inhibitor.

BTK inhibition activities of several compounds among the inventive compounds were randomly tested. The results are shown in Table 2 below.

TABLE 2

Results of BTK inhibition activities of representative compounds

| Compound | BTK $IC_{50}$ (nM) |
| --- | --- |
| 3 | 1.00 |
| 4 | 0.90 |
| 7 | 0.10 |
| 9 | 0.40 |
| 12 | 0.28 |
| 14 | 5.60 |
| 15 | 5.00 |
| 17 | 0.05 |
| 18 | 0.07 |
| 19 | 4.00 |
| 20 | 0.90 |

Experimental Example 2: Histamine Release Assay

According to Kawakami et al., inhibition of BTK activity in mast cells reduces production of a mediator (e.g., histamine), and a lipid mediator, or secretion of cytokine. (Reference [J Immunol. 2000 Aug. 1; 165(3):1210-9. Redundant and opposing functions of two tyrosine kinases, Btk and Lyn, in mast cell activation. Kawakami Y, Kitaura J, Satterthwaite A B, Kato R M, Asai K, Hartman S E, Maeda-Yamamoto M, Lowell C A, Rawlings D J, Witte O N, Kawakami T]).

Histamine release assays were performed with reference to the method disclosed in the article, FEBS Lett. 2002 Sep. 11; 527(1-3):274-8. Silencing of Bruton's tyrosine kinase (Btk) using short interfering RNA duplexes (siRNA). Heinonen J E, Smith C I, Nore B F, and the amount of histamine was measured by an enzyme immunoassay.

The RBL-2H3 cell line, purchased from KCLB (Korean Cell Line Bank), was grown in a DMEM medium supplemented with 10% (v/v) FBS at 37° C. in a 5% $CO_2$ incubator for 72 hours. The cells were transferred into 96-well plates at a density of 10,000 cells/well, and cultured at 37° C. in the 5% $CO_2$ incubator for 24 hours.

The cells were treated with 500 ng/mL of monoclonal anti-DNP (sigma) and each of 0.001, 0.01, 0.1, 1.0 and 10 µM of the test compound in 100% (v/v) dimethyl sulfoxide (DMSO). The cells were treated only with 100% (v/v) DMSO, which was used as a control. The treated samples were cultured at 37° C. in the 5% $CO_2$ incubator for 24 hours. Then, histamine release was measured according to manufacturer's instructions (EIA histamine kit, immunotech). Each well was treated with 50 µL of a histamine release buffer, and allowed to react for 30 minutes at 37° C. Upon completion of the reaction, 100 µL of a sample from each well was transferred to a new plate, and then was thoroughly mixed with 25 µL of an acetylation buffer and 25 µL of an acetylation reagent. 50 µL of the acetylation sample thus prepared was transferred to a plate coated with an antibody, mixed with 200 µL of histamine alkaline phosphatase conjugate, and then allowed to react for 18 hours at 4° C. Once the reaction is completed, the sample from the plate is removed, and then 200 µL of a wash buffer was added to wash three times. 200 µL of a substrate was added thereto, and the mixture was allowed to react at room temperature for 30 minutes. The reaction was terminated by adding 50 µL of a stop solution, and absorbance of the samples was read at 406 nm using Benchmark Plus (Biorad). The histamine release level was calculated based on absorbance of the test group against that of the control group. The $EC_{50}$ (µM) values, in which test compounds reduce the histamine release by 50%, were determined by using Microsoft Excel graphic program.

In order to evaluate efficacies of the inventive compounds as an anti-inflammatory drug, histamine release tests of several compounds among them were randomly conducted. The $EC_{50}$ values of the compounds are summarized in Table 3. The results indicate that the compounds obtained in Examples according to the present invention have excellent efficacy.

TABLE 3

Results of histamine release test of representative compounds

| Compound | Histamine Release $EC_{50}$ (µM) |
| --- | --- |
| 3 | 0.45 |
| 4 | 0.25 |
| 7 | 0.22 |
| 9 | 0.35 |
| 12 | 0.30 |
| 14 | 0.20 |
| 15 | 0.22 |
| 17 | 0.04 |
| 18 | 0.30 |
| 19 | 0.30 |
| 20 | 0.30 |

Experimental Example 3: MTS Assay Based on Anti-Proliferation Assay

MTS assay was performed to evaluate the anti-proliferative activities of the inventive compounds via inhibition on extracellular signal-regulated kinase (Barltrop, J. A. et al., (1991) 5-(3-carboxymethoxyphenyl)-2-(4,5-dimethylthiazoly)-3-(4-sulfophenyl) tetrazolium, inner salt (MTS) and related analog of 3-(4,5-dimethylthiazolyl)-2,5,-diphenyltetrazolium bromide (MTT) reducing to purple water soluble formazans as cell-viability indicators. Bioorg. Med. Chem. Lett. 1, 611-4; Cory, A. H. et al., (1991) Use of an aqueous soluble tertrazolium/formazan assay for cell growth assays in culture. Cancer Comm. 3, 207-12).

Human lymphoma cell lines Jeko-1 (ATCC), Mino (ATCC), H9 (Korean Cell Line Bank) and SR (ATCC), and human leukemia cell lines MV4-11 (ATCC), Molm-13 (DSMZ) and Ku812 (ATCC) were used for the test according to the procedure shown below.

Each of Jeko-1, Mino, H9, SR, MV4-11, Molm-13 and Ku812 cells were transferred into 96-well plates containing RPMI1640 medium (GIBCO, Invitrogen) supplemented with 10% FBS at a density of 10,000 cells/well, and then incubated for 24 hours under conditions of 37° C. and 5% $CO_2$. The wells were treated with each of 0.2, 1, 5, 25 and 100 µM, of the test compounds. The well was treated with DMSO in an amount of 0.08 wt %, which is the same amount as in the test compounds, which was used as a control. The resulting cells were incubated for 48 hours.

MTS assays are commercially available and include the Promega CellTiter 96® Aqueous Non-Radioactive Cell Proliferation Assay. MTS assays were performed in order to evaluate cell viability of the test compounds. 20 µL of a mixed solution of 3-(4,5-dimethylthiazol-2-yl)-5-(3-carboxymethoxyphenyl)-2-(4-sulfophenyl)-2H-tetrazolium, inner salt ("MTS") and phenazine methosulfate (PMS) was added to each well, and then incubated for 2 hours at 37° C. Then absorbance of the samples was read at 490 nm. The anti-proliferation activity level was calculated based on absorbance of the test compounds against that of the untreated control group. The $EC_{50}$ (µM) values, in which test compounds reduce the growth of cancer cells by 50% were calculated.

An assay for anti-proliferation activity was conducted by using Jeko-1, Mino, H9 and SR lymphoma cells so as to evaluate the effectiveness of the inventive compounds as an anti-inflammatory agent as well as an anti-cancer agent. The $EC_{50}$ values thereof are shown in Table 4 below.

TABLE 4

Anti-proliferation assay of the representative compounds against lymphoma cells

| Compound | $EC_{50}$ in Jeko-1 (µM) | $EC_{50}$ in Mino (µM) | $EC_{50}$ in H9 (µM) | $EC_{50}$ in SR (µM) |
|---|---|---|---|---|
| 3 | 0.10 | — | 0.03 | 0.100 |
| 4 | 0.10 | — | 0.03 | 0.030 |
| 7 | 0.03 | 0.018 | 0.007 | 0.015 |
| 9 | 0.03 | — | 0.006 | 0.018 |
| 12 | 0.15 | — | 0.04 | 0.020 |
| 14 | 0.03 | — | 0.02 | 0.018 |
| 15 | 0.10 | — | 0.19 | 0.150 |
| 17 | 0.03 | 0.018 | 0.02 | 0.025 |
| 18 | 0.03 | — | 0.02 | 0.020 |
| 19 | 0.03 | — | 0.04 | 0.020 |
| 20 | 0.03 | — | 0.01 | 0.017 |

Moreover, some inventive compounds that have exhibited excellent efficacies against lymphoma cells were further subjected to an anti-proliferation assay against leukemia cells to confirm their excellent efficacies. The $EC_{50}$ values thereof are shown in Table 5 below.

TABLE 5

Anti-proliferation assay of the representative compounds against leukemia cells

| Compound | $EC_{50}$ in MV4-11 (µM) | $EC_{50}$ in Molm-13 (µM) | $EC_{50}$ in Ku812 (µM) |
|---|---|---|---|
| 7 | 0.002 | 0.003 | 0.600 |
| 17 | 0.004 | 0.012 | 0.190 |

What is claimed is:

1. A method of treating cancer comprising administering to a mammal a compound of formula (I) or a pharmaceutically acceptable salt thereof:

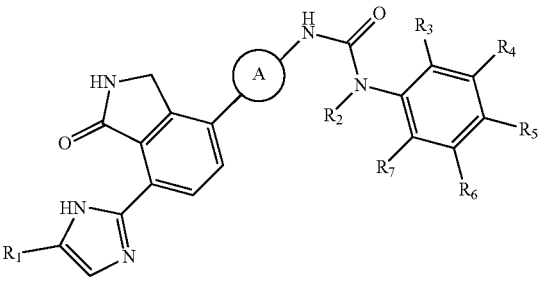

wherein
A is

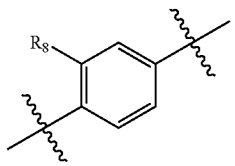

and $R_8$ is hydrogen, fluoro, or methyl;
$R_1$ and $R_2$ are each independently hydrogen or $C_{1-3}$alkyl; and
$R_3$ to $R_7$ are each independently hydrogen or an electron withdrawing constituent, with the proviso that at least two of $R_3$ to $R_7$ are independently an electron withdrawing constituent.

2. The method of claim 1, wherein $R_3$ to $R_7$ are each independently hydrogen, fluoro, chloro, bromo, iodo, cyano, nitro, difluoromethyl or trifluoromethyl.

3. The method of claim 1, wherein $R_8$ is fluoro or hydrogen.

4. The method of claim 1, wherein $R_8$ is fluoro.

5. The method of claim 1, wherein $R_3$ to $R_7$ are each independently hydrogen, fluoro, chloro, bromo, iodo, cyano, difluoromethyl, or trifluoromethyl.

6. The method of claim 5, wherein $R_3$ to $R_7$ are each independently hydrogen, fluoro, chloro, bromo, or iodo.

7. The method of claim 1, wherein $R_1$ and $R_2$ are each independently hydrogen or methyl.

8. The method of claim 1, wherein $R_1$ and $R_2$ are each independently hydrogen or methyl;
wherein $R_3$ to $R_7$ are each independently hydrogen or fluoro, chloro, bromo, and iodo; and $R_8$ is fluoro.

9. The method of claim 8, wherein $R_8$ is fluoro; and $R_3$ to $R_7$ are each independently hydrogen or fluoro.

10. The method of claim 1, wherein $R_1$ and $R_2$ are each independently hydrogen or methyl; $R_8$ is fluoro; and $R_3$ to $R_7$ are each independently hydrogen or fluoro.

11. The method of claim 1, wherein the cancer is selected from the group consisting of lymphoma, leukemia, blood cancer, stomach cancer, non-small cell lung cancer, liver cancer, colorectal cancer, small bowel cancer, pancreatic cancer, brain cancer, bone cancer, melanoma, breast cancer, sclerosing adenosis, uterine cancer, cervical cancer, ovarian cancer, head and neck cancer, esophageal cancer, thyroid cancer, parathyroid cancer, kidney cancer, sarcoma, prostate cancer, urethral cancer, bladder cancer, fibroadenoma, and glioblastoma.

12. The method of claim 11, wherein the cancer is leukemia.

13. The method of claim 11, wherein the cancer is lymphoma.

14. The method of claim 11, wherein the cancer is chronic lymphocytic leukemia (CLL) or small lymphocytic lymphoma (SLL).

15. The method of claim 13, wherein the lymphoma is diffuse large B-cell lymphoma (DLBCL).

16. The method of claim 1, comprising administering an additive selected from the group consisting of an antibiotic, an alkylating agent, an antimetabolite, a hormonal agent, an immunological agent, an interferon-type agent and an anti-cancer agent.

17. The method of claim 1, wherein the compound is 1-{3-fluoro-4-[7-(5-methyl-1H-imidazol-2-yl)-1-oxo-2,3-dihydro-1H-isoindol-4-yl]-phenyl}-3-(2,4,6-trifluoro-phenyl)-urea, or a pharmaceutically acceptable salt thereof.

18. The method of claim 17, wherein the cancer is selected from the group consisting of lymphoma, leukemia, blood cancer, stomach cancer, non-small cell lung cancer, liver cancer, colorectal cancer, small bowel cancer, pancreatic cancer, brain cancer, bone cancer, melanoma, breast cancer, sclerosing adenosis, uterine cancer, cervical cancer, ovarian cancer, head and neck cancer, esophageal cancer, thyroid cancer, parathyroid cancer, kidney cancer, sarcoma, prostate cancer, urethral cancer, bladder cancer, fibroadenoma, and glioblastoma.

19. The method of claim 18, wherein the cancer is leukemia.

20. The method of claim 18, wherein the cancer is lymphoma.

21. The method of claim 18, wherein the cancer is chronic lymphocytic leukemia (CLL) or small lymphocytic lymphoma (SLL).

22. The method of claim 20, wherein the lymphoma is diffuse large B-cell lymphoma (DLBCL).

* * * * *